(12) United States Patent
Wee

(10) Patent No.: US 8,224,588 B2
(45) Date of Patent: Jul. 17, 2012

(54) METHOD AND APPARATUS FOR MEASURING THE CONDUCTIVITY OF THE WATER FRACTION OF A WET GAS

(75) Inventor: Arnstein Wee, Randaberg (NO)

(73) Assignee: Multi Phase Meters AS, Forus (NO)

( * ) Notice: Subject to any disclaimer, the term of this patent is extended or adjusted under 35 U.S.C. 154(b) by 838 days.

(21) Appl. No.: 12/226,804

(22) PCT Filed: May 2, 2007

(86) PCT No.: PCT/NO2007/000153
§ 371 (c)(1),
(2), (4) Date: Dec. 10, 2008

(87) PCT Pub. No.: WO2007/129901
PCT Pub. Date: Nov. 15, 2007

(65) Prior Publication Data
US 2009/0088985 A1    Apr. 2, 2009

(30) Foreign Application Priority Data
May 2, 2006  (NO) .................................. 20061947

(51) Int. Cl.
*G01N 31/00* (2006.01)
(52) U.S. Cl. .......................................................... 702/30
(58) Field of Classification Search .............. 702/30–32, 702/38, 45, 49, 50, 100, 189; 324/640, 694
See application file for complete search history.

(56) References Cited

U.S. PATENT DOCUMENTS

| | | | |
|---|---|---|---|
| 4,201,083 A | 5/1980 | Kurita et al. | 73/861.06 |
| 4,402,230 A | 9/1983 | Raptis | 73/861.04 |
| 4,423,623 A | 1/1984 | Ho et al. | 73/61.41 |
| 4,458,524 A | 7/1984 | Meador et al. | 73/61.43 |
| 4,459,958 A | 7/1984 | Latapie | 123/406.37 |
| 4,638,672 A | 1/1987 | McCall | 73/861.52 |
| 4,862,060 A | 8/1989 | Scott et al. | 324/639 |
| 4,902,961 A * | 2/1990 | De et al. | 324/640 |

(Continued)

FOREIGN PATENT DOCUMENTS
WO          94/17373         8/1994
(Continued)

OTHER PUBLICATIONS
International Search Report dated Jul. 24, 2007.
(Continued)

*Primary Examiner* — Mohamed Charioui
(74) *Attorney, Agent, or Firm* — Nields, Lemack & Frame, LLC

(57) ABSTRACT

A method for determining the water conductivity of a multi-component mixture of gas and at least one liquid containing water in a pipe, the method comprising the following steps: a. electromagnetic measurements at least two measurement frequencies are performed in a pipe near the pipe wall at a first cross-sectional location where the mixture predominantly contains gas and at a second cross-sectional location where the mixture predominantly contains liquid, b. the temperature of the multi-component mixture is determined, and c. based on an empirically determined relationship between the measurements performed is step a and b and the conductivity of pure water, the conductivity of the water contained in the multi-component mixture is determined. An apparatus for performing the method is also disclosed.

22 Claims, 10 Drawing Sheets

U.S. PATENT DOCUMENTS

| | | | |
|---|---|---|---|
| 4,974,452 A | 12/1990 | Hunt et al. | 73/861.64 |
| 4,976,154 A | 12/1990 | Schneider et al. | 73/861.06 |
| 5,103,181 A | 4/1992 | Gaisford et al. | 324/637 |
| 5,107,219 A | 4/1992 | Marrelli et al. | 324/640 |
| 5,135,684 A | 8/1992 | Mohn et al. | 261/76 |
| 5,331,284 A | 7/1994 | Jean et al. | 324/639 |
| 5,341,100 A | 8/1994 | Taylor | 324/341 |
| 5,351,521 A | 10/1994 | Cracknell | 73/19.1 |
| 5,455,516 A | 10/1995 | Jean et al. | 324/639 |
| 5,576,974 A | 11/1996 | Marrelli et al. | 702/179 |
| 5,701,083 A | 12/1997 | Goldberg et al. | 324/642 |
| 5,793,216 A | 8/1998 | Constant | 324/639 |
| 6,009,760 A | 1/2000 | Jakkula et al. | 73/861.06 |
| 6,109,097 A | 8/2000 | Conrads et al. | 73/61.41 |
| 6,332,111 B1 | 12/2001 | Fincke | 702/50 |
| 6,335,959 B1 | 1/2002 | Lynch et al. | 378/45 |
| 6,378,380 B1 | 4/2002 | Kusters et al. | 73/861.63 |
| 6,466,035 B1 | 10/2002 | Nyfors et al. | 324/634 |
| 6,755,086 B2 | 6/2004 | Salamitou et al. | 73/861.04 |
| 6,898,986 B2 | 5/2005 | Daniel et al. | 73/861.63 |
| 6,993,979 B2 | 2/2006 | Segeral | 73/861.64 |
| 2003/0011386 A1* | 1/2003 | Xie et al. | 324/694 |
| 2004/0244501 A1 | 12/2004 | Nyfors et al. | 73/861.63 |

FOREIGN PATENT DOCUMENTS

| | | |
|---|---|---|
| WO | 00/45133 | 8/2000 |
| WO | 03/012413 | 2/2003 |
| WO | 03/034051 | 4/2003 |
| WO | 2005/057142 | 6/2005 |
| WO | 2006/019311 | 2/2006 |

OTHER PUBLICATIONS

Norweigan Search Report dated Feb. 7, 2007.

* cited by examiner 37  38  39  40

41  42  43  44

METHOD AND APPARATUS FOR MEASURING THE CONDUCTIVITY OF THE WATER FRACTION OF A WET GAS

BACKGROUND

The present invention relates to a method and apparatus for determining the water conductivity of a multi-component mixture of gas and at least one liquid containing water in a pipe.

A flowing mixture of oil, water and gas or condensate, water and gas is a common occurrence in the oil industry being a product of an unprocessed well stream. Such a well stream is often referred to as a multiphase mixture where oil or condensate, water and gas are referred to as individual phases or fractions. When the amount of gas (GVF) is greater then 90% of the total volume in the pipe, the well is often referred to as a wetgas well. However, most wetgas wells have a GVF above 97% and it is common with GVFs in the range 99.7-99.9%.

The formation water in the hydrocarbon reservoir is typical saline water, and its salinity is usually known to the operator. Under normal situations, the well should not produce any formation water. In fact, formation water in the pipeline can cause hydrate and scale formation in addition to severe pipeline corrosion. If the amount of formation and fresh water (also referred as total water fraction) in a well is known to the field operator, chemical inhibitors can be injected into the well stream in order to limit the unwanted effects due to the water. Alternatively, the production rate from the well can be changed in order to minimize or reduce the formation water production or shut down the well completely to spare the pipeline infrastructure. It is of particular interest to measure the formation and fresh water content of remotely operated subsea wells since the cost of the pipelines in such an installation is severe. It is common for most subsea installations to commingle wells into a common pipeline and transporting the multiphase fluid to a process facility. Such a process facility may be located several hounded kilometers from the seabed installation leading to long multiphase transportation pipes on the seabed. Consequently, it may take many months to detect and identify a well producing saline water without an apparatus as described in the present invention installed at the wellhead on the seabed. If the saline water production of a remote subsea well is particularly high, it may even be necessary to shut down the well in order to avoid damage of the pipeline infrastructure. Knowing the total water (formation water plus fresh/condensed water) fraction and the water salinity, the fresh water and formation water fraction of the well can be determined since the salinity of the formation water is known to the operator. In order to fulfill the requirements of the field operator, an instrument for measuring at least the water conductivity/water salinity of the wells would be need. The water fraction can either be calculated based on a compositional analysis of the wet gas and using PVT (pressure volume temperature) correlations for calculation of the water fraction, alternatively the water fraction can be measured as described in one of the embodiment of this invention providing a more accurate determination of the water flow rate. In order to obtain safe and economical operation of the equipment at the seabed, the operator typical needs to know the salt content of the water fraction with a resolution in the range of 0.1%-0.5% NaCl by weight in the water fraction, and the water fraction of the wet gas with a resolution in the range 0.01-0.1% of the total volume of the pipe.

Many wetgas wells have a gas fraction (GVF) of 97-99.9% with a water fraction in the range 0.005-1%. However, there is also water present as vapor in the gas. For changing pressures and temperatures, some of the water vapor in the gas may be condensing to form liquid water. The mass of the vapor water in the pipe may be many times greater then the mass of the liquid water in the pipe. In addition the dielectric constant of vapor water is significantly higher (3-4 times) than the dielectric constant for the same mass of water as liquid phase. Consequently, the dielectric constant of a hydrocarbon mixture containing vapor water may be 10-20 times greater than the dielectric constant of a hydrocarbon mixture containing the same mass of water as liquid. Vapor water is of low importance to the operator since it does not influence scaling, waxing or corrosion of the pipelines to the same extent as saline water. However knowing the liquid water fraction and the salt content of the liquid water fraction is very important as outlined above, and hence vapor water adds to the challenge of measuring the liquid water fraction and water salinity since the ratio between the amount of water as liquid and amount of water as vapor also is pressure and temperature dependent. Consequently, small variations in the pressure and temperature, associated with changing flow rates or back pressure due to changing pressure drops in the transportation pipelines, can greatly influence the dielectric constant of the hydrocarbon mixture to a much greater extent than variations in the water fraction of the multiphase mixture. The dielectric constant of the gas is normally a calibration constant for instruments performing measurement of the water fraction of a wetgas. The dielectric constant of gas determines the zero point of the measurement of the water fraction. Hence, phase transition from liquid water to vapor water and vice versa influences the zero point of the water fraction measurement making reliable measurements at low water fractions even more difficult.

Microwaves are widely used for measurement of composition and water salinity of a multiphase mixture. U.S. Pat. No. 4,458,524 (1984) discloses a multiphase flow meter that measures the dielectric, density, temperature and pressure. Such device uses phase shift between two receiving antennas to determine the dielectric constant. Other techniques are further known being based on resonance frequency measurement. Examples of such techniques are disclosed in WO3/034051 and U.S. Pat. No. 6,466,035. U.S. Pat. No. 5,103,181 describe a method based on measurement of constructive and destructive interference patterns in the pipe.

However, none of the above described methods are able to measure both the water fraction and water salinity of a multiphase mixture, and all the devices above are highly influenced by any changes in the dielectric and density properties of the gas and oil.

It is also well known that the composition and dielectric loss (i.e. the complex dielectric constant) of a multiphase mixture can be measured based on measurement of resonance frequency and quality factor of a resonant cavity. The method disclosed in WO 03/012413 measures the composition and describes a method where the composition and dielectric loss of a multiphase mixture is derived based on measurement of resonance frequency and quality factor of two resonant devices placed at two different locations in a pipe. The two devices have different resonance frequencies. Hence the method relies on accurate power/loss measurement for a transmitted and received microwave signal. It is also well known that the complex dielectric constant of a media can be measured by measuring the phase shift and attenuation of an electromagnetic wave through the media. U.S. Pat. No. 5,793,216 describe a method and apparatus for characterization of a multiphase mixture based on transmission and reception of microwaves. The method is based on measurement of phase shift and power attenuation at several measurement frequencies. The antennas are located in the cross section of the pipe at several cross sections of the pipe. U.S. Pat. No. 4,902,961 describe a method for measuring complex dielectric constant based on measurement of phase shift and power attenuation. The measurement is performed at two different (fixed) frequencies, one in the X-band and the other in the S-band. Other examples can be found in NO 200 10 616 which discloses a method for measurement of the water conductivity of the continuous phase of a multiphase mixture based on a power and phase measurement at microwave frequencies, U.S. Pat. No. 5,341,100 describing a method and apparatus for measurement of fluid conductivity and hydrocarbon volume based on a measurement of phase shift and attenuation (power) of an electromagnetic wave and U.S. Pat. No. 5,107, 219 describing a method and apparatus for measurement of the conductance of a fluid based on measurement of microwave energy (power/loss) and phase difference.

There are two main disadvantages with the above mentioned devices and methods. First, a change in the dielectric constant of the gas due to variations in the water vapor content or variations in the gas density influences the dielectric constant of the gas. As a consequence, the zero calibration point for the water fraction measurement is changing causing unacceptable measurement errors. Secondly, the above methods and apparatuses have limited ability to sense small variations and provide accurate and repeatable measurements since they rely on an accurate power or loss measurement at only one frequency or a few (two) fixed frequencies. Accurate power and loss measurements at microwave frequencies at one frequency or two fixed frequencies are difficult to perform partly due to impedance mismatch, which is very common for any microwave based industrial device for measuring dielectric constant, and partly due to limitations of the electronics itself. Consequently, the limitations of the measurement electronics and standing waves due to impedance mismatches make it difficult to obtain the required accuracy, repeatability and sensitivity for accurate water conductivity and/or water fraction measurements.

It is also well known that the composition of the multiphase mixture can be measured based on a measurement of the cut-off frequency of the pipe. Examples of such devices are found in U.S. Pat. Nos. 4,423,623, 5,455,516, 5,331,284, 6,614,238, 6,109,097 and 5,351,521 describing methods for determining the composition of a multiphase mixture based on a measurement of the cut-off frequency of a pipe based on loss or phase measurements at a varying frequency. NO 20043470 describes a method an apparatus for determining water salinity based on phase measurement(s) only. However, all these devices are highly influenced by changes in the dielectric constant of the gas due to variations in the water vapor content or variations in the gas density which both have a large influence on the dielectric constant of the gas. Devices based on measurement of conductance or resistance is also known for measurement of water conductivity and water fraction. However, these devices are highly affected by oil contamination isolating the measurement signal from the process since these measurements are normally performed at very low frequencies. Drift in the electronics due to temperature variations and aging is also a common problem with such devices. Consequently, such devices are not suited for high precision measurements of water conductivity and water fraction of a wet gas stream. All the above mentioned devices also require a flowing multiphase fluid in order to be able to perform the measurement. This means that the devices can not provide accurate measurement at stationary conditions in the pipe.

As mentioned above, all the previously mentioned devices require accurate information of gas and oil/condensate density and the dielectric constant of gas and oil (condensate). These data are a function of temperature and pressure and may also change significantly over the life of the well due to commingling of fluid from multiple production zones of a well. Multiple production zones means that the well produces from different layers in the ground and the composition of the hydrocarbon and water may be different for the various zones. In practice it is also quite often difficult to obtain accurate estimate of these calibration inputs, particularly for wells producing from multiple production zones in the ground.

Devices for measuring the flow rates of a multiphase fluid are well known. Such devices may be based on cross correlation of a measurement signal detecting variations in liquid and gas droplets of the flow. By transmitting a carrier into the flow and measuring the response, the received signal contain information of the variations in the flow caused by amplitude (loss), phase or frequency modulation by the disturbances (in-homogeneities) of the flow. By performing the measurements at two sections of the pipe located at a known distance, one can create two time varying signals that are shifted in time equal to the time it takes the multiphase flow to travel between the two sections. Example of such devices are disclosed in U.S. Pat. No. 4,402,230, U.S. Pat. No. 4,459,958, U.S. Pat. No. 4,201,083, U.S. Pat. No. 4,976,154, WO94/17373, U.S. Pat. No. 6,009,760 and U.S. Pat. No. 5,701,083

Other devises for measurement of flow rates may be based on measurement of differential pressures across a restriction in the pipe such as a venturi, orifice, v-cone or flow mixer. Examples of such devices can be found in U.S. Pat. Nos. 4,638,672, 4,974,452, 6,332,111, 6,335,959, 6,378,380, 6,755,086, 6,898,986, 6,993,979, 5,135,684, WO 00/45133 and WO03/034051.

It is the purpose of this invention to overcome the above mentioned limitations of existing solutions.

It is the purpose of this invention to perform accurate measurements of the salinity and/or conductivity of the water phase of a multiphase mixture containing small amounts of water.

It is the purpose of this invention to perform accurate measurements of the water salinity/water conductivity with a minimum of calibration parameters.

It is the purpose of the invention to provide accurate measurements of the water fraction of a multiphase mixture containing small amounts of water.

It is the purpose of this invention to perform accurate measurements of the conductivity of the water fraction of a wet gas with large variations in the dielectric properties of the gas.

It is the purpose of this invention to perform accurate measurements of the conductivity of the water fraction of a wet gas with large variations in the density of the gas.

It is the purpose of this invention to perform accurate measurements of the conductivity of the water fraction of a wet gas without the need for any flow through the apparatus.

It is the purpose of this invention to perform accurate measurements of the conductivity of the water fraction of a wet gas with large variations in the dielectric properties of the oil/condensate.

It is the purpose of this invention to perform accurate measurements of the conductivity of the water fraction of a wet gas with large variations in the density of the oil/condensate.

It is the purpose of this invention to perform accurate measurements of the conductivity of the water fraction of a wet gas at low water salinities.

It is the purpose of this invention to perform accurate measurements of the water salinity and water fraction and compensate the measurements for any variations in the dielectric or density properties of the gas.

It is the purpose of this invention to perform accurate measurements of the water salinity and water fraction and compensate the measurements for any variations in the dielectric or density properties of the oil/condensate.

It is the purpose of the invention to provide liquid hold-up in the apparatus such that the properties of the liquid phase can be measured more accurately.

It is the purpose of the invention to detect liquid hold-up in the apparatus.

It is the purpose of the invention to provide separation of the liquid and gas phases of a multiphase mixture such that more accurate measurements of the liquid phase can be obtained.

It is the purpose of the invention to provide a non-intrusive device for performing the measurements.

It is the purpose of the invention to provide a compact mechanical structure for performing the measurements.

SUMMARY

These purposes are obtained according to the invention by a method comprising the following steps:
a. electromagnetic measurements at least two measurement frequencies are performed in a pipe near the pipe wall at a first cross-sectional location where the mixture predominantly contains gas and at a second cross-sectional location where the mixture predominantly contains liquid,
b. the temperature of the multi-component mixture is determined, and
c. based on an empirically determined relationship between the measurements performed in step a and b and the conductivity of pure water, the conductivity of the water contained in the multi-component mixture is determined.

The apparatus according to the invention is further characterized by the features as defined in the independent claim 15.

Dependent claims 2-14 and 16-22 define preferred embodiments of the invention.

The present invention is based on broad band electromagnetic measurements performed in two different locations of a horizontal pipe with a flowing or stationary multiphase fluid containing water and gas. The two measurements are preferable performed in a wider passage of a horizontal pipe in order to provide holdup of liquids in the apparatus. The frequency range is typical in the range 1 Mhz-10 Ghz. The preferred arrangement is to have one transmitter and receiver pair located in the top of a wider passage of a horizontal pipeline and a second transmitting and receiver pair located in the bottom of the wider passage of the pipeline as shown in FIG. 1. The transmitter and receiver pair at the top of the pipe is performing measurements predominantly in the gas phase of the multiphase fluid and the transmitter and receiver pair in the bottom is performing measurements predominantly in the liquid or water phase of the multiphase fluid. The extension of the pipe diameter serves to provide liquid hold-up around the antennas in the bottom of the pipe such that the measurements can be performed on a larger portion of the liquid(s). The method can also be used with a double receiver pair in the top and the bottom of the pipe for performing differential measurements. In such an arrangement, the method and apparatus can be extended for measurements of higher water conductivities and water fractions. Reflection methods such as transmission and measurement of reflected electromagnetic energy of an open ended coaxial probes or radar techniques based on transmission and reception of a reflected electromagnetic pulse from the pipe, can also be used to perform the broad band measurements at the top and the bottom of the pipe. The measurements at the bottom of the horizontal pipe are compared to the measurements at the top of the horizontal pipe in order to determine the water conductivity and water fraction. The measurement at the top and at the bottom of the pipe can also be compared to verify that there is separation of the liquid and gas phases in the apparatus. If no separation is taking place, operational actions such as changing the flow rates of the well, can be performed in order to obtain liquid and gas separation in the apparatus. Alternatively, the method as described in NO 2004 3470 based on measurement on the complex dielectric constant of the multiphase mixture can be used to determine the water fraction and water conductivity under such circumstances. Electromagnetic energy is then transmitted on antenna 7 of FIG. 2 and the phase difference on the antennas 6 and 8 are used to derive the water fraction and water conductivity.

However, the method of NO 2004 3470 will not provide as high measurement resolution as the present invention based on separation. The apparatus can also be extended to determine the flow rate(s) of the multiphase mixture.

The uniqueness of the present invention is the ability to provide accurate measurements of the water fraction and water salinity/conductivity of a hydrocarbon multiphase mixture containing small amounts of water. Furthermore, the method allows for variations in the dielectric constant of the gas due to variations in the amount of vapor water in the gas. The measurements of water conductivity and water fraction can be done with a minimum of additional devices since only a temperature measurement is required in addition to the electromagnetic measurements. Furthermore, the method and apparatus provides hold-up of liquid in the measurement section such that the liquid phase can be measured with a higher precision. The method allows for detection of liquid hold-up in the measurement which can be used to verify that the meter operates according to its designed conditions. The method also provides accurate measurements of the water salinity and water fraction despite large variations in the gas and condensate densities greatly simplifies calibration of the device.

BRIEF DESCRIPTION OF THE DRAWINGS

The invention will be further described in the following with reference to the figures, where.

DETAILED DESCRIPTION

Below is a summary of the main elements involved in determining the conductivity of the water and the water volume fraction of the multiphase mixture.

Figure 2:
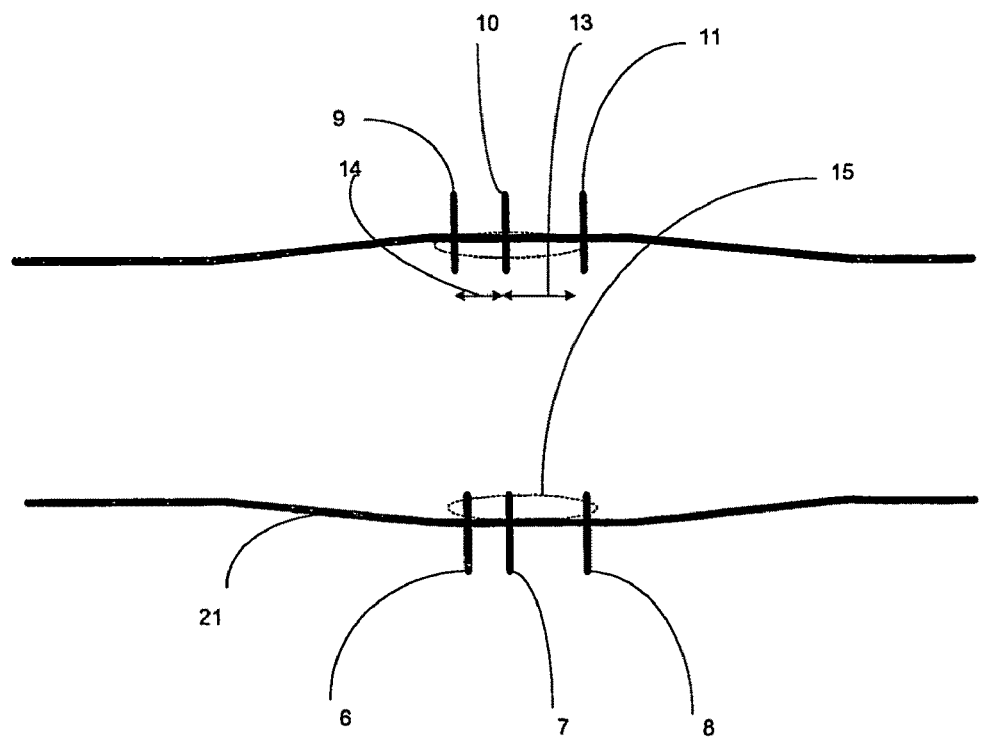
FIG. 2 shows a schematic longitudinal sectional view of an exemplified embodiment of an apparatus for measuring the volume fraction and water conductivity according to the invention.
Figure 5:
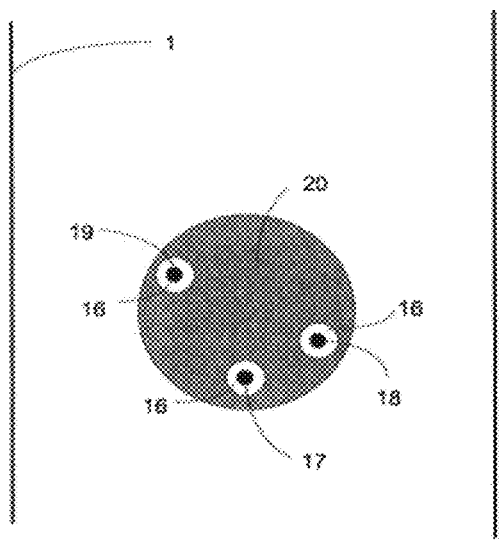
FIG. 5 shows at a larger scale a plan portion view of FIG. 2.

Electromagnetic measurements are performed using a sending antenna 2 and receiving antenna 3 located in the bottom of a wider section of a horizontal pipe 1 and a sending antenna 4 and receiving antenna 5 located in the top of the same section of the pipe 1. The antennas penetrate slightly into the pipe 1. The apparatus, or sensor, may also be constructed as shown in FIG. 2 where a sending antenna 7 and two receiving antennas 6, 8 are located in the bottom of a wider section of a horizontal pipe 12 and a sending antenna 10 and two receiving antennas 9, 11 are located in the top of the same section of the pipe 1. The two receiving antennas 11, 9 are located different distances 13, 14, from the sending antenna 10. The same antenna configuration is used in the bottom of the pipe. The antennas may be made as one compact probe unit 20 as shown in FIG. 5 where the transmitting antenna 17 and the two receiving antennas 18, 19 are electrical insulated from the metal housing 20 by ceramic glass 16.

Figure 3:
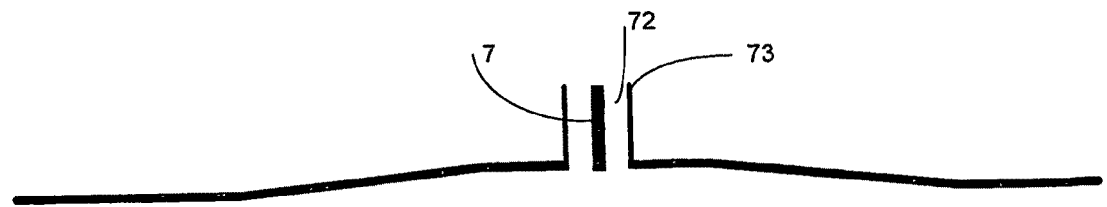
FIG. 3 shows a schematic longitudinal sectional view of an exemplified embodiment of an apparatus for measuring the volume fractions and water conductivity according to the invention.
Figure 3:
Figure 4:
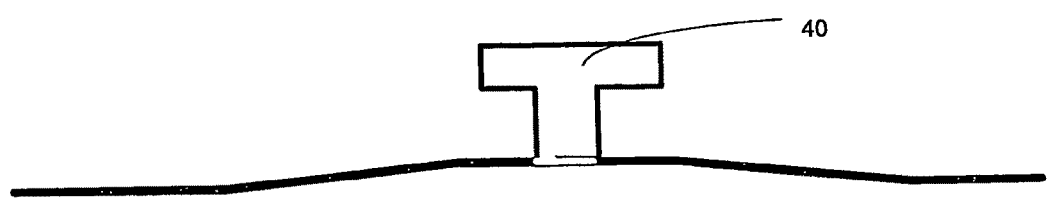
FIG. 4 shows a schematic longitudinal sectional view of an exemplified embodiment of an apparatus for measuring the volume fractions and water conductivity according to the invention.
Figure 4:
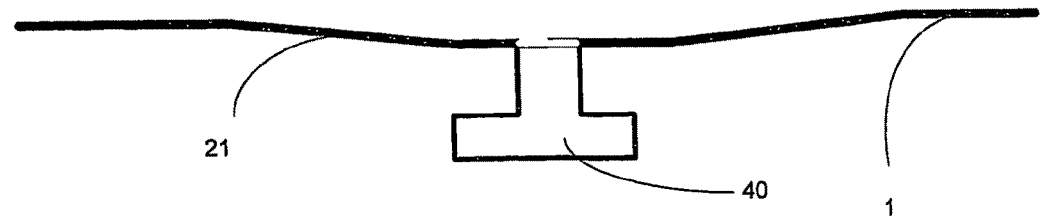

The electromagnetic broad band measurements may also be performed based on transmission of electromagnetic energy on an open ended coaxial conductor 7 and measuring the characteristics of the reflected signal. The transmitted signal may either be a pulse or a sinusoidal signal. One open ended coaxial conductor is then placed at the top of the pipe and another coaxial conductor is placed at the bottom of the pipe as shown in FIG. 3. The electromagnetic broad band measurement may also be performed by transmission of an electromagnetic pulse from an antenna 40 through an opening (slot) in the pipe and measuring the characteristics of the reflected pulse as shown in FIG. 4.

It is well known that measurement of small component fractions of a multiphase mixture is extremely demanding. However, the measurement uncertainty reduces as the component fraction increases compared to the total volume of the pipe. A horizontal pipe also functions as a gravity separator separating the multiphase mixture and hence creates a higher concentration of liquids in the bottom of the pipe and a higher concentration of gas at the top of the pipe. Additional holdup of liquid can be provided by expanding the pipe diameter at the location of the measurement devices. Then there will be a higher concentration of liquid around the antennas located in the bottom of the pipe 1 and predominantly gas around the antennas located at the top of the pipe 1. Hence, the liquid concentration around the measurement device in the bottom is higher compared to the average liquid fraction of the pipe. A gradual increase and decrease of the diameter 21 is preferred; however a step change may also be used. With a gradual change of diameter less than 7 degrees angle, turbulent flow in the sensor can be avoided. Turbulent flow may disturb separation of the liquid and gas phases in the sensor.

By performing electromagnetic measurements of loss or phase over a broad frequency spectrum (1 Mhz-10 Ghz) with the antennas located in the bottom of the pipe and comparing the result with similar measurements performed with the antennas at the top of the pipe, the water fraction and water conductivity/salinity are determined. By performing the same measurements in the top and the bottom of the pipe, the apparatus is also able to compensate the measurements for any variations in the properties of the gas phase such as water vapor content or changes in the gas density due to pressure changes in the pipeline. The method is also very little affected by changes in the density of the oil or condensate such that accurate water fraction measurements can be performed without any precise information regarding hydrocarbon densities avoiding the use of a device for measuring the pressure in the pipe for compensation purposes. The measurement at the top and at the bottom of the pipe can also be compared to verify that there is separation of the liquid and gas phases in the apparatus. If no separation is taking place, operational actions such as changing the flow rates of the well, can be performed in order to obtain liquid and gas separation. The temperature and pressure of the multiphase mixture can also be measured. Only a temperature measurement is required in order to obtain the desired functionality since pressure variations only have a small effect on the water fraction measurement and a marginal effect on the measurement of the water conductivity. However, a pressure transmitter can be used to further improve the measurements if extremely high precision is required for the water fraction measurement. For simplicity these devices has been omitted from the drawings and will not be further discussed in the description of the new invention.

Figure 6:
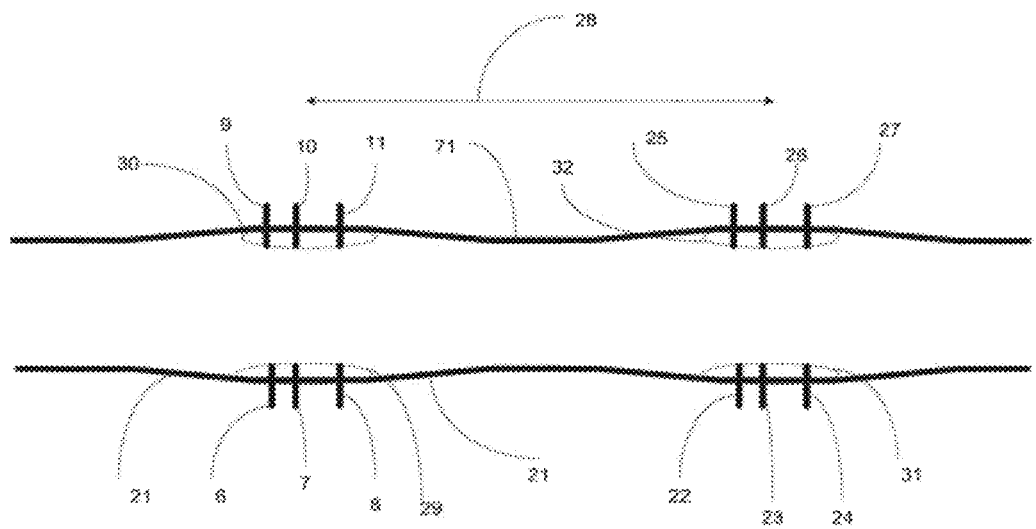
FIG. 6 shows a schematic longitudinal sectional view of an exemplified embodiment of an apparatus for measuring the volume fractions, flow rates and water conductivity according to the invention.

Two devices may also be combined in order to derive the flow rates of the multiphase mixture as shown in FIG. 6. The two devices (sensors) are separated by a known distance 28. By performing simultaneous measurements with the antenna pairs 6,7, 8 and antenna pairs 22,23, 24, and cross correlating these measurements, it is possible to obtain a measurement of the velocity of the liquid flowing in the bottom of the pipe. Similar measurements can be performed with the antenna pairs 9,10,11 and 25,26,27 for the gas phase. Measurements between the upper antenna pairs 30 and lower antenna pairs 29 in the cross section of the pipe can also be combined to measure the velocity by cross correlating these measurements with the same measurements performed between the upper antenna pairs 32 and lower antenna pairs 31. The cross sectional measurement can then be performed by transmitting on antenna 7 and receiving on antenna 9 and 11. Similarly, transmitting on antenna 10 and receiving on antenna 6 and 8. When a signal, also called a carrier, is transmitted into the flow, the gas and liquid bubbles in the flow creates variations, or modulations of the carrier which are detected at the receiving end. The measurement signal can be constructed such that the disturbances of the flow creates both amplitude (loss) modulations, phase modulations or frequency modulations of the transmitted carrier which can be used for cross-correlation purposes. The configuration of FIG. 6 allows for use of high measurement frequencies since the pipe section 71 serves as a high-pass filter due to the higher cut-off frequency of the pipe section 71 compared to the pipe section around the antennas. It is well known that the scatter loss due to spreading of the carrier by liquid droplets increases greatly with frequency, consequently, the measurement sensitivity to small disturbances such as liquid droplets in the gas is greater with a high frequency carrier compared to a low frequency carrier.

Figure 7:
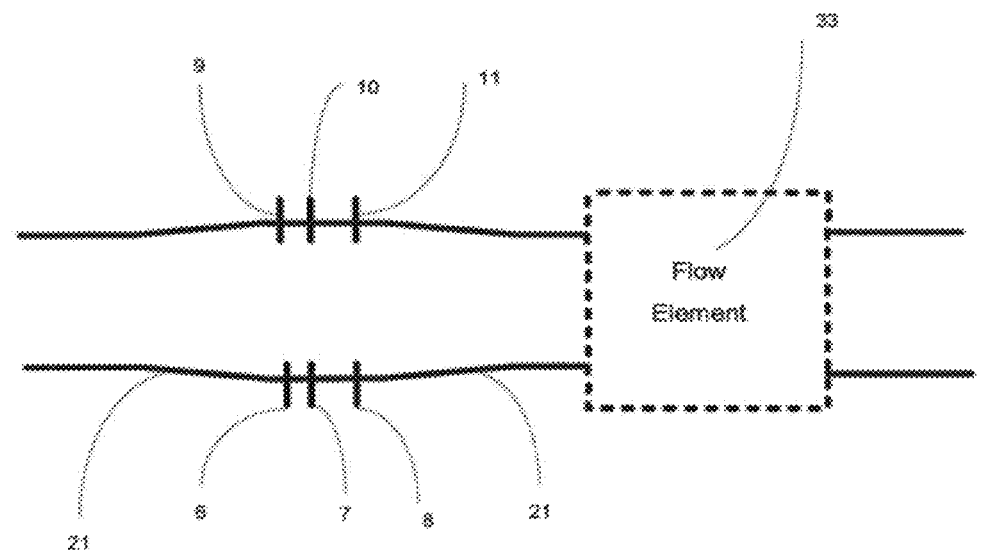
FIG. 7 shows a schematic longitudinal sectional view of an exemplified embodiment of an apparatus for measuring the volume fractions, flow rates and water conductivity according to the invention.

The apparatus may also be combined with flow element 33 such as a venturi, v-cone or orifice plate for determination of liquid(s) and gas flow rates as shown in FIG. 7.

Figure 8:
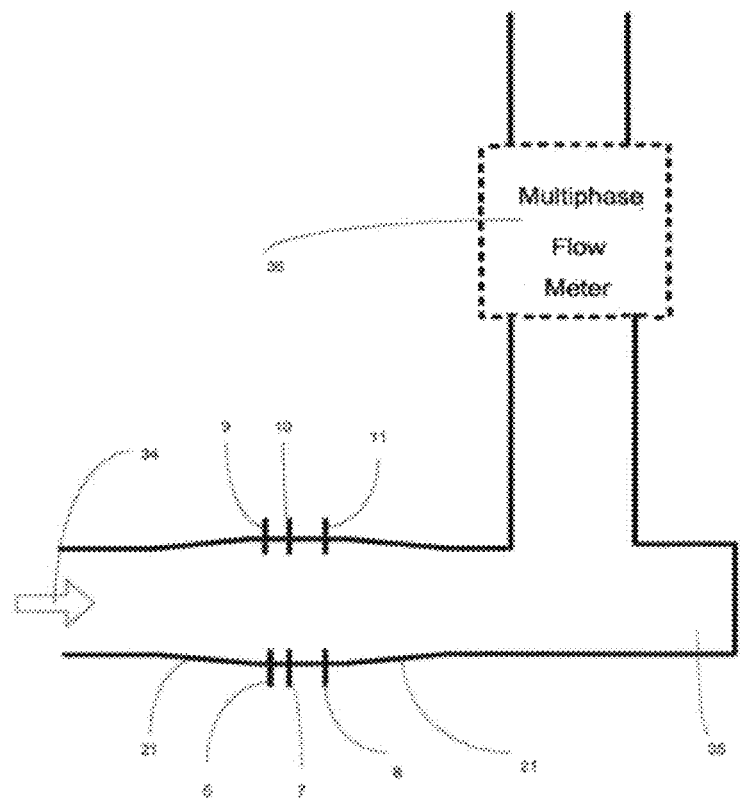
FIG. 8 shows a schematic longitudinal sectional view of an exemplified embodiment of an apparatus for measuring the volume fractions, flow rates and water conductivity according to the invention.

The apparatus may also be combined with a multiphase flow meter 36 as described in WO 2005/057142 installed in a vertical section of the pipe as shown in FIG. 8. It is then common to install the multiphase meter downstream a blind T 35. The flow direction is now shown with an arrow 34.

Below is a more detailed description of the invention:

The fundamentals of electromagnetic waves traveling any-media and the behavior of electromagnetic filed in a pipe (waveguide) is well described in the literature (e.g. *Fields and Waves in Communication Electronics* by S. Ramo, J. R. Whinnery and T. V. Duzer—1984). Electromagnetic measurement principles and methods for modeling and analyzing the measurement signals are also well described in "*Microwave Electronics—measurements and material characterization*" by Chen et al, (Wiley), "*Electromagnetic mixing formulas and applications*", by Ari Sihvola, (IEE Electromagnetic Wave Series 47), and "Aqueous Dielectrics" by J. B. Hasted (Chapman and Hall).

The general equation for the electric field of a positively traveling electromagnetic wave in free-space with x and y components of the electric field traveling in the direction z can be described by the following equation:

$$E=(\hat{x}E_1+\hat{y}E_2e^{j\psi})e^{-jkz} \quad \text{Equation 1}$$

where:
E=Electric field vector
$E_1$=Electric field in x direction
$E_2$=Electric field in y direction
ψ=Phase angle between x and y component
k=Phase constant or wave number For an electromagnetic wave traveling in a lossy medium such as a mixture of oil and/or gas dispersed in water, the wave number k becomes a complex number as shown in equation 2 below.

$$k=\alpha+j\beta \quad \text{Equation 2}$$

where:
α=Wave attenuation coefficient
β=Wave phase constant

The exponential propagation factor for phasor waves, $e^{-jkz}$, of equation 1 then becomes, $$e^{-jkz}=e^{\alpha z}e^{-j\beta z} \quad \text{Equation 3}$$

Where α and β can be calculated according to equation 4 and 5 below:

$$\alpha = \omega\sqrt{\left(\frac{\mu\varepsilon'}{2}\right)\left[\sqrt{1+\left(\frac{\varepsilon''}{\varepsilon'}\right)^2}-1\right]} \quad \text{Equation 4}$$

$$\beta = \omega\sqrt{\left(\frac{\mu\varepsilon'}{2}\right)\left[\sqrt{1+\left(\frac{\varepsilon''}{\varepsilon'}\right)^2}+1\right]} \quad \text{Equation 5}$$

where:
∈'=Real part of the complex dielectric constant for the media
∈"=Imaginary part of the complex dielectric constant for the media
ω=Frequency
μ=Permeability of the media,
where complex dielectric constant E of the media can be described according to equation 6 below:

$$\in=\in'-j\in'' \quad \text{Equation 6}$$

For air, gas, oil and condensate, the imaginary part of the dielectric constant is for all practical purposes zero. For water, the complex dielectric constant can be described by a single Debye relaxation law as shown below:

$$\varepsilon_{water} = \varepsilon_\infty + \frac{\varepsilon_s - \varepsilon_\infty}{1+j\omega\tau} - j\frac{\sigma_{water}}{\omega\varepsilon_0} \quad \text{Equation 7}$$

where:
$\in_{water}$=Complex dielectric constant of water
$\in_\infty$=Dielectric constant at infinite frequencies
$\in_s$=Static dielectric constant
ω Frequency
$\sigma_{water}$=Conductivity of water
$\in_0$=Boltzmann's constant Equation 7 can be re-arranged for calculation of the real (∈') and imaginary (∈") part of the dielectric constant of water as shown in equation 8 and 9 below:

$$\varepsilon' = \frac{\varepsilon_s - \varepsilon_\infty}{1+(\omega\tau)^2} \quad \text{Equation 8}$$

$$\varepsilon'' = \frac{\varepsilon_s - \varepsilon_\infty}{1+(\omega\tau)^2}(\omega\tau) + \frac{\sigma_{water}}{\omega\varepsilon_0} \quad \text{Equation 9}$$

where:
$\in_s$=Static dielectric constant
$\in_\infty$=Dielectric constant at infinite frequency
$\sigma_{water}$=Conductivity of water τ=Dipole relaxation time
ω=Frequency
∈₀=Boltzmann's constant Measurements and equations of the static dielectric constant of water, the dipole relaxation time and dielectric constant at infinite frequencies are well described in the literature. Some examples can be found in J. B. Hasted which has performed a critical review of available data in Aqueous Dielectrics (1973). More recent data has been published by Udo Kaatze in *J. Chem. Eng. Data*, 1989p 371-374 and Meissner and Wentz in *Report from Boeing/AER investigation for CMIS* and "*A formulation for the Static Permittivity of Water and Steam at temperatures from* 238 *K to* 873 *K at Pressures up to* 1200 *Moa, Including Derivates mid Debye-Hünckel Coefficients*" by D. P. Fernandez et al J. Phys. Chem. Ref. Data, Vol. 26, No 4, 1997

There is also evidence that the static dielectric constant of water, the dipole relaxation time and the dielectric constant at infinite frequencies also are dependent of the salinity of the water. The static dielectric constant of water, the dipole relaxation time and the dielectric constant at infinite frequencies for fresh water can then be multiplied by a water salinity dependent correction factor in order to obtain the values of $\epsilon_s$, $\epsilon_\infty$, and τ for saline water. Some examples of the equations for the water salinity correction factor for $\epsilon_s$, $\epsilon_\infty$ and τ has been published by Meissner and Wentz in *Report from Boeing/AER investigation for CMIS page* 17 and J. B. Hasted, *Aqueous Dielectrics* (1973).

Figure 9:
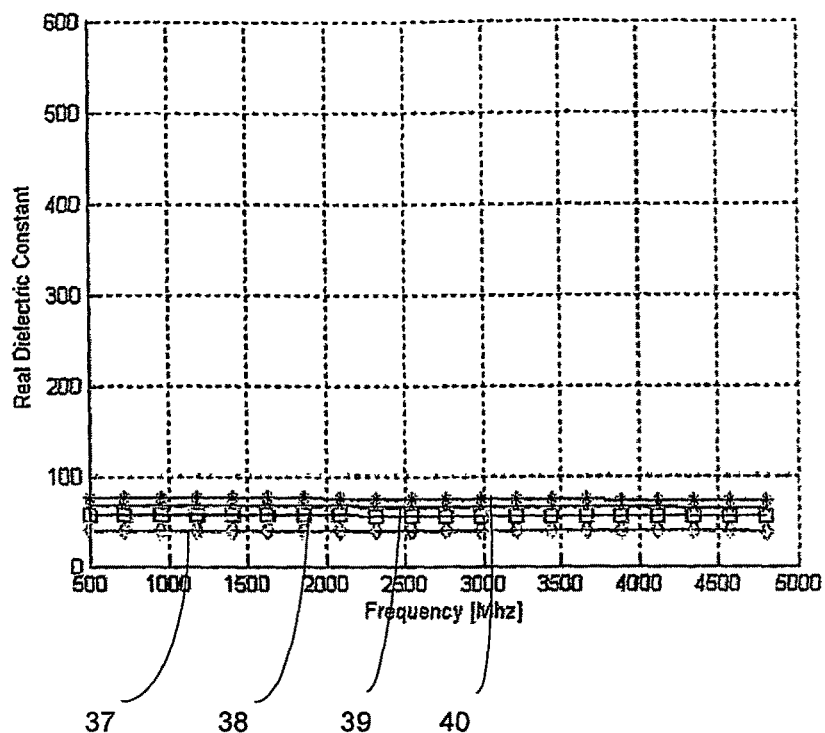
FIG. 9 shows a graph of the real part of the dielectric constant for water.
Figure 10:
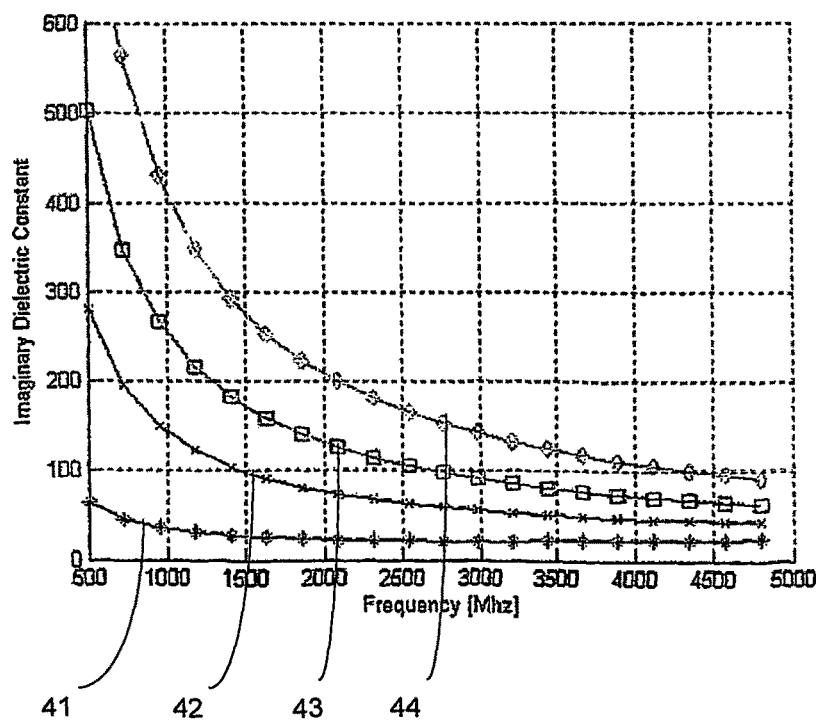
FIG. 10 shows a graph of the imaginary part of the dielectric constant for water.

FIG. 9 shows a graph of the real part of the dielectric constant for saline water (NaCl salt) at 25° C. according to equation 8 with a salinity of 1%, 5%, 10% and 20% NaCl by weight 37 38 39 40. FIG. 10 shows a graph of the imaginary part of the dielectric constant for saline water at 25° C. according to equation 9 with a salinity of 1%, 5%, 10% and 20% NaCl by weight 41 42 43 44 plotted on the same scale as FIG. 9. By comparing FIGS. 9 and 10 it is clear that the value of imaginary part of the dielectric constant of saline water is much more affected by a change in the salinity or frequency compared to the real part of the dielectric constant and hence by performing measurement at a broad frequency range, the imaginart part of the dielectric constant can be discriminated from the real part of the dielectric constant.

The effective real part of the complex dielectric constant is:

$$\varepsilon_{eff} = \frac{\varepsilon'}{2} * \left\{ 1 + \sqrt{1 + \left(\frac{\varepsilon''}{\varepsilon'}\right)^2} \right\} \quad \text{Equation 10}$$

Where:
∈': Real part of dielectric constant
∈": Imaginary part of dielectric constant In mixture models the dielectric permittivity of a multiphase mixture is expressed in terms of the effective real part of the dielectric constant of every constituting component and their volume fraction. Several comprehensive reviews of dielectric mixture models have been published in the literature, van Beek, 1967; Ting a at al., 1973; Wang & Schmugge, 1980; Shutko & Reutov, 1982; Hallikainen et al., 1985; Sihlova, 1989 and "*Flow permittivity models and their applications in multiphase meters*", by E. Hammer, Proc. Multiphase Metering, IBC Technical Services, Mar. 12-13, 1997, Aberdeen. The Hanai-Bruggeman equation, originally derived by Bruggeman (1935) and later modified to yield complex dielectric constants by Hanai (1936), relates the dielectric constant of a two component mixture to the volume fractions of the components. If the two component mixture is droplets as an inner phase dispersed in a continuous media of an outer phase, the equation become:

$$\frac{\varepsilon_{inner} - \varepsilon_{mix}}{\varepsilon_{inner} - \varepsilon_{outer}} * \left(\frac{\varepsilon_{outer}}{\varepsilon_{mix}}\right)^{\frac{1}{3}} = 1 - \frac{\phi_{inner}}{\phi_{inner} + \varphi_{outer}} \quad \text{Equation 11}$$

where:
$\epsilon_{inner}$=Dielectric constant of the inner phase (dispersed phase)
$\epsilon_{outer}$=Dielectric constant of the outer phase (continuous phase)
$\epsilon_{mix}$=Measured dielectric constant of the mixture
$\Phi_{inner}$=Volume fraction of inner phase (dispersed phase)
$\Phi_{outer}$=Volume fraction of outer phase (continuous phase)

Figure 1:
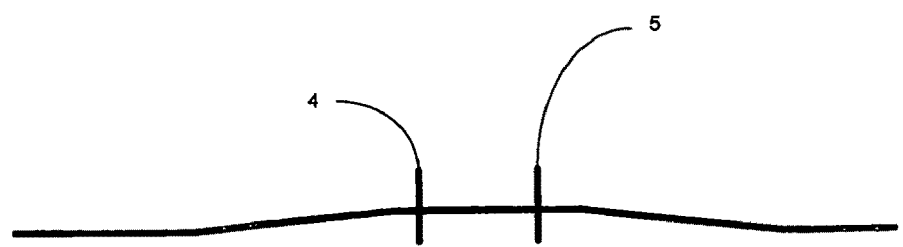
FIG. 1 shows a schematic longitudinal sectional view of an exemplified embodiment of an apparatus for measuring the water conductivity according to the invention.
Figure 1:
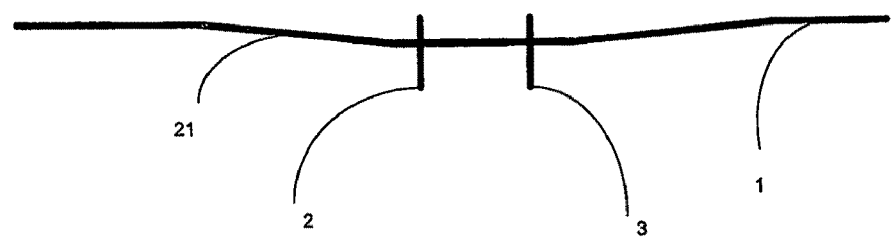
Figure 11:
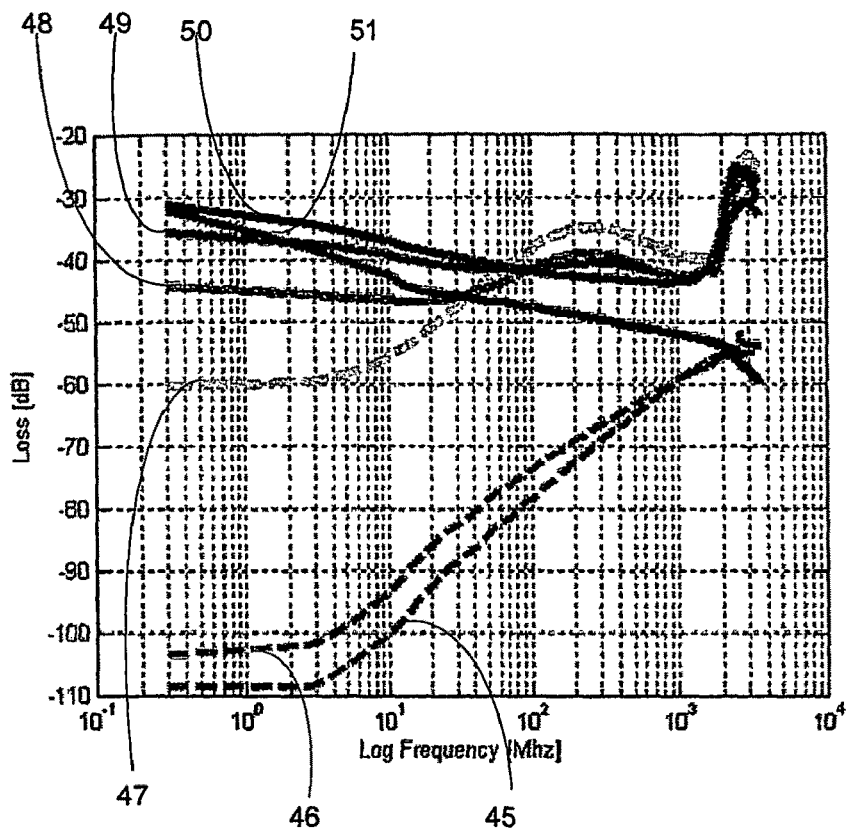
FIG. 11 shows a graph of the measured loss of the apparatus of FIG. 1.

Hence, by measuring the dielectric constant of a multiphase mixture and knowing the effective dielectric constant of the individual components of the mixture such as water and hydrocarbon, the, volume fraction of water and hydrocarbon can be calculated. Dielectric properties for hydrocarbons can be found in: "*Handbook of Chemistry and Physics*" (CRC Press) and "*Complex permittivity of crude oils and solutions of heavy oil fractions*", by Friisø et al, in Journal of Dispersion Sci. Technology, 19(1), (1998) page 93-126 and FIG. 11 shows the measured loss vs. frequency for the sensor of FIG. 1 for the antennas in the bottom of the pipe for air (gas) 45, oil, 46, fresh water 47 and saline water with a water salinity of 0.1%, 0.5%, 1.5% and 16% respectively 48 49 50 51. The gas fraction (GVF) is in this case 99% with a corresponding liquid fraction of 1% of the total volume in the sensor. All the liquid is located in the bottom of the pipe. As seen on the curves of FIG. 11, the loss in the low frequency region is much larger with gas, oil or fresh water in the sensor compared to the low frequency loss with some salt in the water. Even a small change in the water salinity of 0.1% NaCl causes a change of more than 15 dB of loss in the low frequency region. The change in loss in the low frequency is twofold. Without any salt in the liquid, the coupling between the antennas is purely capacitive which favors transfer of energy at higher frequencies between the antennas. The coupling efficiency between the antennas is determined by the area of the antennas, the dielectric constant of the medium between the antennas and the frequency. In the frequency of interest (below 10 Ghz), the dielectric constant of oil, fresh water and gas is almost constant in the entire frequency region.

However, the capacitive coupling between the antennas increases with frequency due to the increased capacitive coupling at higher frequencies and the fact that the antennas become more efficient at smaller wavelengths. The antennas of the sensor are in effect dipoles which are inserted into the pipe. The length of the antennas are just a few mm, such that one wavelength corresponds to a frequency far above 10 Ghz. The aperture or coupling efficiency of a dipole antenna is given by the equation:

$$A = \frac{3}{8\pi}\lambda^2 \quad \text{Equation 12}$$

Where:
A: Antenna aperture (coupling efficiency)
λ: Wavelength Hence, from equation 12 it can be seen that the coupling efficiency increases with 3 dB for every doubling of the frequency of the transmitted signal.

When the water phase contains salt and the liquid phase is water continuous, the liquid becomes conductive. This can occur either by separation, i.e. that water is flowing in the bottom of the pipe with a layer of condensate or oil on top, or if the water fraction is large enough such that the oil is dispersed as droplets in a continuous water phase. The latter typical occurs for water fractions above 30% for a water/condensate mixture.

When the liquid becomes conductive, the shape of the loss curve 48, 49, 50, 51, changes. Although a conductive liquid phase introduces more loss at all frequencies, the variation in the frequency spectrum is different with a conductive liquid compared to a non conductive liquid.

The coupling of the antenna to the medium between the antennas is more efficient with a conductive media since the area of the antennas and wavelength of the transmitted signal is of less importance for conductive coupling. This effect benefits particular the coupling efficiency at low frequency. However, the media itself is now lossier, such that the loss between the antennas with a conductive media is higher. This loss is highly frequency and salinity dependent due to the frequency and salinity dependence of the imaginary part of the dielectric constant of water as shown in FIG. 10. Hence for a water continuous liquid containing salt, the ratio between the loss at high and low frequencies are much smaller compared to the ratio between the loss at high and low frequencies for a water continuous liquid containing no salt.

The broad band loss ratio R (or just loss ratio), which for the context of this patent application is defined as measured loss at a high frequency band divided by measured loss at a low frequency band, can be used to derive the water salinity or conductivity of the water. The loss ratio R is obtained by performing a sweep in the low frequency range of the frequency spectrum and averaging all the loss measurements and similarly performing a sweep in a high frequency band and averaging all the loss measurements performed in this band. R is obtained by dividing the two average readings. The sweep should at least contain two measurements chosen such that the distance between the frequencies is equal to one period of the frequency of the overlaying ripple pattern caused by standing waves occurring in the cables of the measurement path. By doing so, the effect of standing wave patterns can be minimized. By using more frequencies over a broader frequency range for the upper and lower sweep, the unwanted effect due to standing waves in the measurement path can be further reduced. The width of the frequency sweep should preferable be a multiple of the frequency period for the standing waves.

By rearranging equation 1, the loss ratio R can be calculated as:

$$R = \frac{PT_H * e^{-\alpha_H^* Z}}{PT_L * e^{-\alpha_L^* Z}} \qquad \text{Equation 13}$$

Where
R: Broad band loss ratio
$PT_H$: Transmitted high frequency energy
$PT_L$: Transmitted low frequency energy
$\alpha_H$: Attenuation coefficient at high frequency
$\alpha_L$: Attenuation coefficient at low frequency
Z: Distance between the transmitting and receiving antennas.

The attenuation coefficients can be calculated using equation 4. For air, the attenuation coefficients are approximately zero. Hence, by measuring the broadband loss ratio R in air, equation 13 becomes:

$$R = K1 * \frac{e^{-\alpha_H^* Z}}{e^{-\alpha_L^* Z}} \qquad \text{Equation 14}$$

where
K1: Measured broadband loss ratio in air
When R and K1 is given in decibels (dB), equation 14 becomes:

$$R = \frac{20 * z * (\alpha_L - \alpha_H) * K1}{\ln(10)} \qquad \text{Equation 15}$$

The effect of variations in the dielectric properties of the gas due to varying amount of vapor water mass in the gas and the effect of any density changes in the gas can effectively be removed by normalizing the measurement at the bottom of the pipe to the measurement at the top of the pipe as shown in equation 15. This is done by dividing the measurement of the broadband loss ratio at the bottom of the pipe with the broadband loss ratio measured at the top of the pipe. This normalization also reduces measurement caused by discrepancies in the frequency spectrum of the electronics and cables.

$$R_{Normalized} = \frac{R_{Lower}}{R_{Upper}} \qquad \text{Equation 16}$$

The normalized broad band loss ratio can also be used to verify that separation and hold-up of liquid is occurring in the apparatus, where a value of for $R_{Normalised}=1$ means that no separation is taking place.

Figure 12:
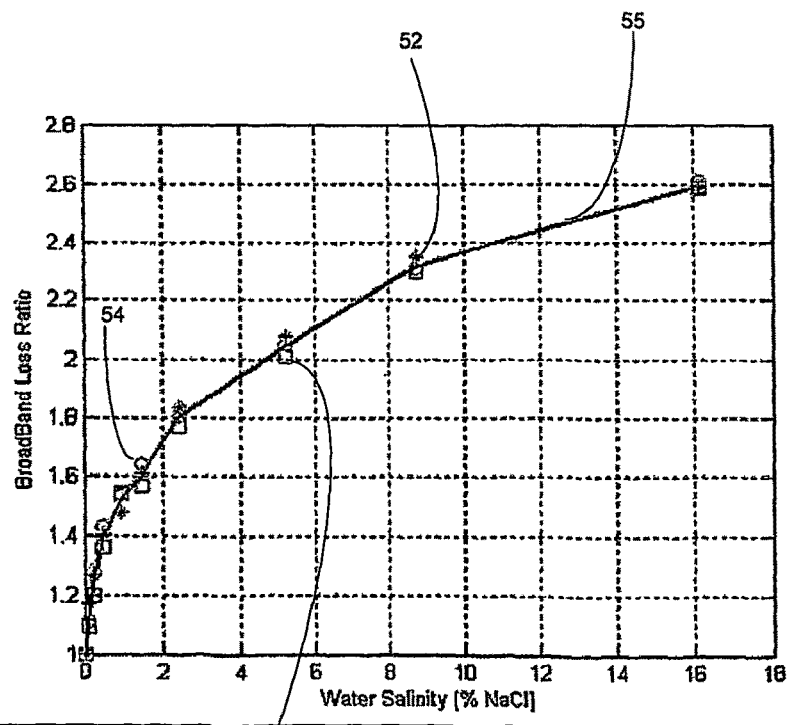
FIG. 12 shows a graph of the normalized measured broad band loss ratio vs. the water salinity for the apparatus of FIG. 1.

FIG. 12 shows a graph of the measured normalized broadband loss ratio vs the water salinity for a gas fraction of 99.3%, 98.6% and 97.2% gas respectively 52, 53, 54. The curve 55 is obtained by interpolating the average measurement of 52, 53 and 54 vs. water salinity. I.e., based on a measured value of the normalized broadband loss ratio and using the empirically derived calibration curve 55, the salinity of the water can be derived. The simplest way to derive the calibration curve 55 is to fill the device partly or completely with water with varying salinity and record the measured normalized broadband loss ratio. The measured values can then be curve fitted to obtain a suitable curve or equation relating the normalized broadband loss ratio to the salinity of the water of the multiphase mixture.

Figure 13:
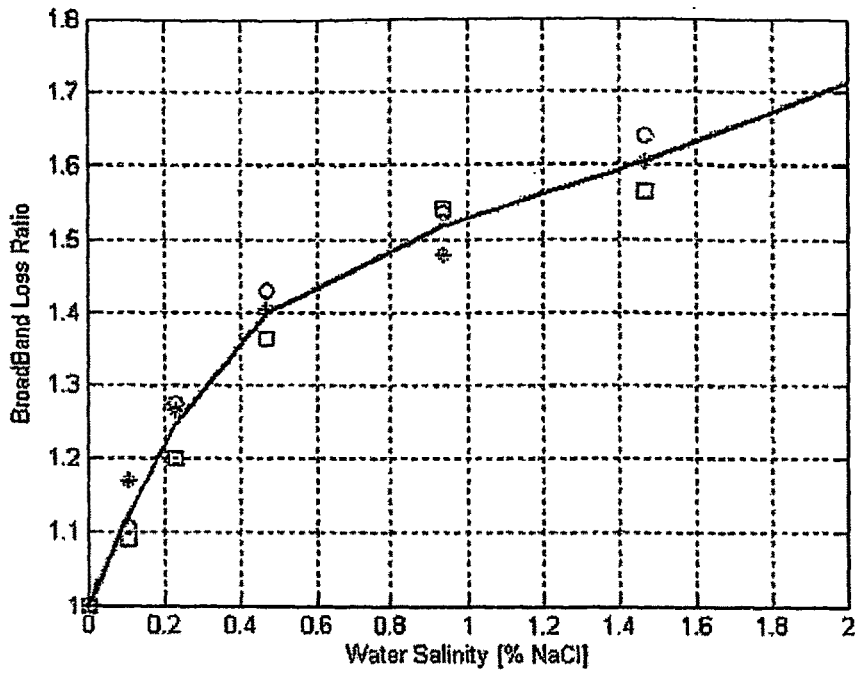
FIG. 13 shows a graph of the measured normalized broad band loss ratio vs. the water salinity for the apparatus of FIG. 1.

Equation 15 can be used to derive the complex dielectric constant for the liquid based on a measurement of the normalized R. The complex dielectric constant is derived by adjusting the real and imaginary part of the dielectric constant of equation 4 until the right hand side of equation 15 matches the left hand side of equation 15. This is a straight forward process; however, it is a bit more challenging since the value of Z is a function of the wavelength of the transmitted signal since the receiving antenna is located in the near field from the transmitter. However, empirical tests have revealed that experimental derived calibration curves can be used for low water salinities. FIG. 13 shows the lower salinity range of the data displayed in FIG. 12. As seen on the graph, the curve is fairly steep in the lower region and the measurements of the broadband loss ratio falls around the same values irrespective of the amount of liquid in the sensor. In the region below 1% NaCl in the water phase, an empirical derived calibration curve can be used which is derived based on measurement of the broadband loss with different amounts of liquid in the sensor and is almost unaffected by the amounts of oil in the water as long as the liquid is water continuous. This curve can also be used for higher water salinities, however the measurement uncertainty will then be greater since the slope of the curve is lower.

However, two different methods can be used with the apparatus of FIG. 2. For water salinities below 0.5% say, the above mention method based on measurement of broadband loss ratio can be used. For water salinities above 0.5%, the measurement can be based on a measurement of the complex dielectric constant of the multiphase mixture. The complex dielectric constant is determined by measuring the wave phase constant β of a plane electromagnetic wave propagating near the inside wall of the pipe. The measurement of β is based on a measurement of the phase difference between the two receiving antennas 6 8, inside the pipe located at different distances from a third transmitting antenna 7. The phase measurement is performed at least two frequencies in the range between 1 Mhz and 10 Ghz.

The dielectric constant of water is, amongst other, a function of the water conductivity and measurement frequency. However, since the water fraction is independent on both water conductivity and measurement frequency, the water conductivity can be determined by performing a water fraction measurement at least two different measurement frequencies and adjusting the water conductivity of equation 9 until the water fraction calculated according to equation 11 gives the same value at all measurement frequencies.

Figure 17:
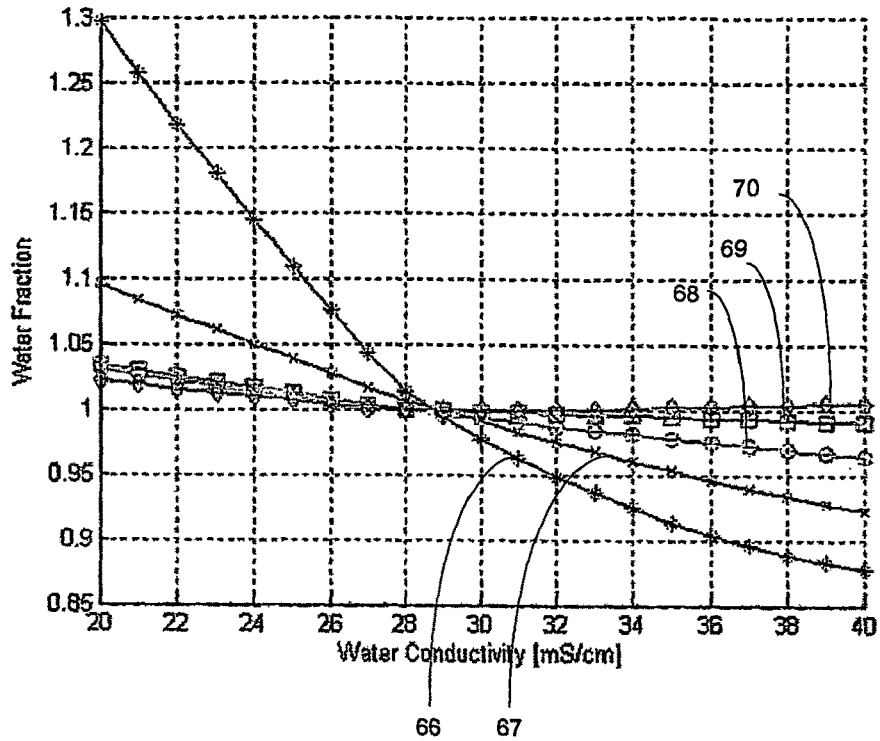
FIG. 17 shows a graph of the measured water fraction for a wide water conductivity range and 5 different measurement frequencies for a typical flowing fluid with a continuous water phase and saline water.

The two receiving antennas 6 and 8 are located at distances $d_1$ 14 and $d_2$ 13 from the transmitting antenna 7. Optimum dimension of $d_1$ are in the range 8-12 mm and for $d_2$ optimum dimension will typical be twice the dimension of $d_1$. Typical the antennas will penetrate a few mm into the pipe. The phase difference between the antennas 6 and 8 is measured for at least two frequencies transmitted on the sending antenna 7. The frequencies should also be selected such that there is sufficient difference in the imaginary part of the dielectric constant between the highest and lowest frequency such that the slope of the water fraction measurement vs. conductivity curve, as shown in FIG. 17, differs sufficient to obtain the required sensitivity on the water fraction standard deviation calculation of FIG. 18. The frequency range could also be selected based on an optimization rule for utilizing the full dynamic measurement range of the electronics. The frequencies are typical selected in the range 20-5.000 Mhz, however frequencies in the range 1 Mhz to 10 Ghz may be used. The ratio between the lowest and highest frequency will be dependent of the choice of measurement frequencies and capabilities of the measurement electronics. Provided that there is sufficient loss inside the pipe at the area close to the antennas, the propagating electromagnetic wave between the sending antenna 7 and receiving antennas 6 and 8 will behave according to plane wave theory. In this context, sufficient loss will typical imply a water continuous multiphase mixture where the conductivity of the water at the given temperature is above approximately 8 mS/cm. A conducting water film along the pipe wall, which frequently occurs in wet gas wells, may also provide sufficient loss such that the propagating wave between the transmitting and receiving antennas behave according to plane wave theory.

According to plane wave theory, the phase difference between the receiving antennas 2 and 3 can be described as:

$$\Delta\varphi = \beta * Z \qquad \text{Equation 17}$$

where:
  $\Delta\varphi$=Phase difference between receiving antennas 2 and 3
  β=Propagating wave phase constant (ref. equation 5)

$Z=d_2-d_1$
  $d_1$=Distance from sending antenna 7 to receiving antenna 6
  $d_2$=Distance from sending antenna 7 to receiving antenna 8

Hence, by measuring the phase difference Δφ and knowing the value of Z for the system, the phase constant β for the wave propagating from the sending to the receiving antennas can be determined. Experiments have shown that the value of Z is also a function of the wavelength of the transmitted signal and there is also a slight dependence on the conductivity of the liquid. This is due to the fact that the receiving antennas are located in the near field of the transmitting antenna and the model for plane wave propagation is then not completely valid. This behavior can be modeled by introducing a frequency dependent term as shown in equation 19 below:

$$\chi = \frac{\beta}{\omega} \qquad \text{Equation 19}$$

Where:
  β=Propagating wave phase constant (ref. equation 5)
  ω=frequency (rad)

χ can then be calculated from the measured phase difference, measurement frequency and value of Z according to equation 20 below:

$$\chi = \frac{\Delta\varphi}{Z\omega} \qquad \text{Equation 20}$$

Combining equation 5, 17, 19 and 20 provides the following equation for the real (∈') and imaginary (∈") part of the dielectric constant within the pipe.

$$\chi = \sqrt{\left(\frac{\mu\varepsilon'}{2}\right)\left[\sqrt{1+\left(\frac{\varepsilon''}{\varepsilon'}\right)^2}+1\right]} \qquad \text{Equation 21}$$

A some what simpler way to calibrate the measurement has been found by using a phase dependent calibration factor Z. This is due to the fact that the effective antenna distance Z is a function of the transmitted wavelength which again is a function of the measured phase difference between the two receiving antennas. The effective distance Z is also dependent on the multiphase conductivity and Z can then be calculated as shown below:

$$Z = f(\Delta\varphi, \sigma_{mix}) \qquad \text{Equation 22}$$

Figure 16:
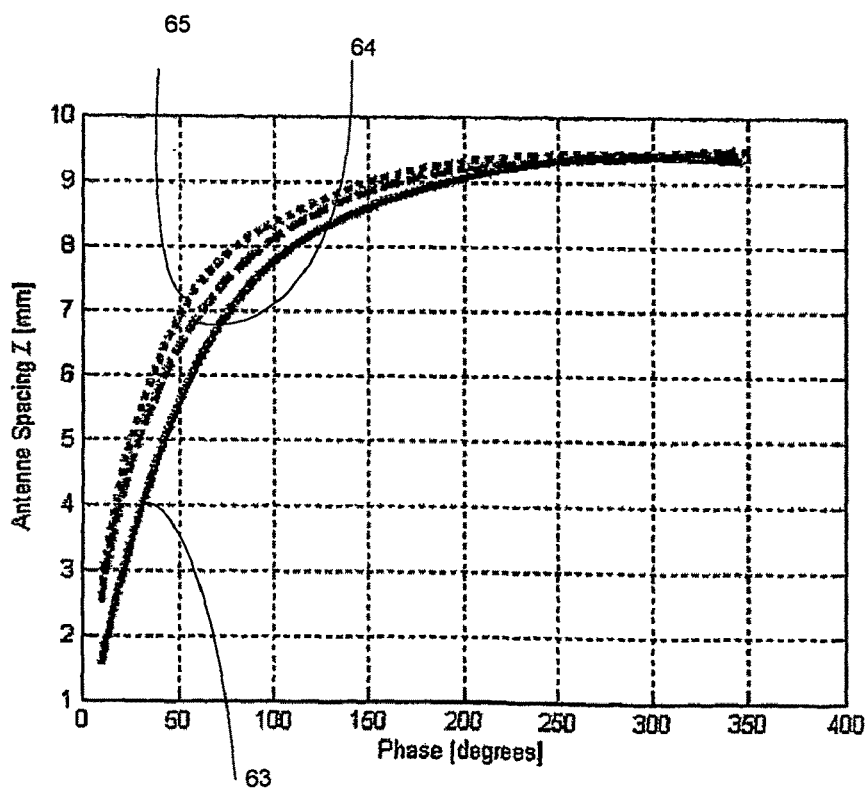
FIG. 16 shows a graph of the calibration factor Z vs. phase for the apparatus of FIG. 2.

Where:
  Z: Effective antenna distance (calibration constant)
  Δφ: Measured phase difference
  $\sigma_{mix}$: Conductivity of the multiphase mixture Examples of such functions are shown in FIG. 16 with water salinity of 0.47%, 5.21%, and 16.08% respectively. The appropriate curve is selected based on the measured water conductivity and the measured phase difference defines the point on the curve. Interpolation between the curves can be used for intermittent conductivities.

The conductivity of the oil/water mixture can be calculated according to the Maxwell Garnett mixing formula as shown below:

$$\sigma_{mix} = \sigma_{water} + 3 * \phi_{oil} * \sigma_{water} * \frac{\sigma_{oil} - \sigma_{water}}{\sigma_{oil} - 2 * \sigma_{water} - \phi_{oil} * (\sigma_{oil} - \sigma_{water})} \quad \text{Equation 23}$$

Where:
$\sigma_{mix}$: Conductivity of the oil water mixture
$\sigma_{oil}$: Conductivity of the oil
$\sigma_{water}$: Conductivity of the water
$\phi_{oil}$: Fraction of oil in the liquid phase The complex dielectric constant can be determined in an iterative calculation loop. Assuming a constant ratio between the real and imaginary part of the dielectric constant when performing these iterations simplifies the calculations. Experiments have shown that the ratio between the real and imaginary dielectric constant for pure water applied to a mixture of water and oil, provides accurate calculations of the volume fraction. This approximation introduces only small measurement errors since the Bruggeman mixing formula is fairly linear function.

Hence, the ratio between the real and imaginary dielectric constant is defined as:

$$K = \frac{\varepsilon''_{water}}{\varepsilon'_{water}} \quad \text{Equation 24}$$

The real part of the dielectric constant for the mixture can then be calculated by combining equation 24 and 5 as shown below:

$$\varepsilon' = \frac{2 * \beta^2}{\omega^2 * (\sqrt{1 + K^2} + 1) * \mu} \quad \text{Equation 25}$$

Figure 14:
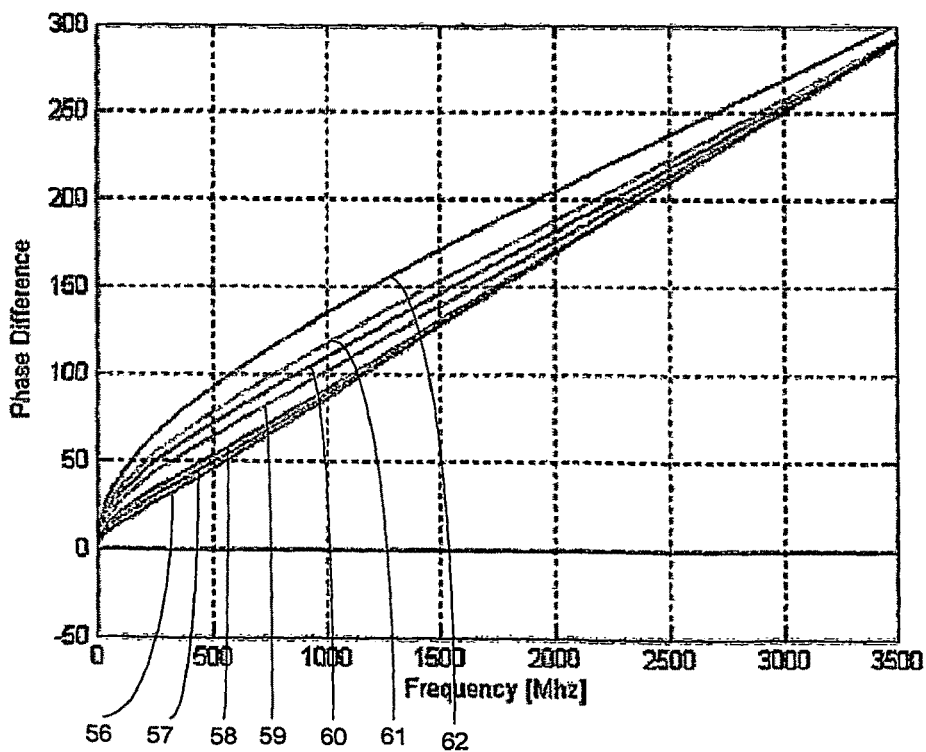
FIG. 14 shows a graph of the theoretical phase difference vs. frequency for the apparatus of FIG. 2.

FIG. 14 shows the theoretical phase difference at the receiving antennas for a plane wave traveling from the sending antenna to the receiving antennas for Z=0.008. The phase difference is calculated in a frequency range from 0.1 to 3.500 Mhz with a water fraction of 1.0 and a water salinity of 1%, 1.75%, 2.5%, 5%, 7%, 9% and 15% salt (NaCl) 56 57 58 59 60 61 62 by weight.

Figure 15:
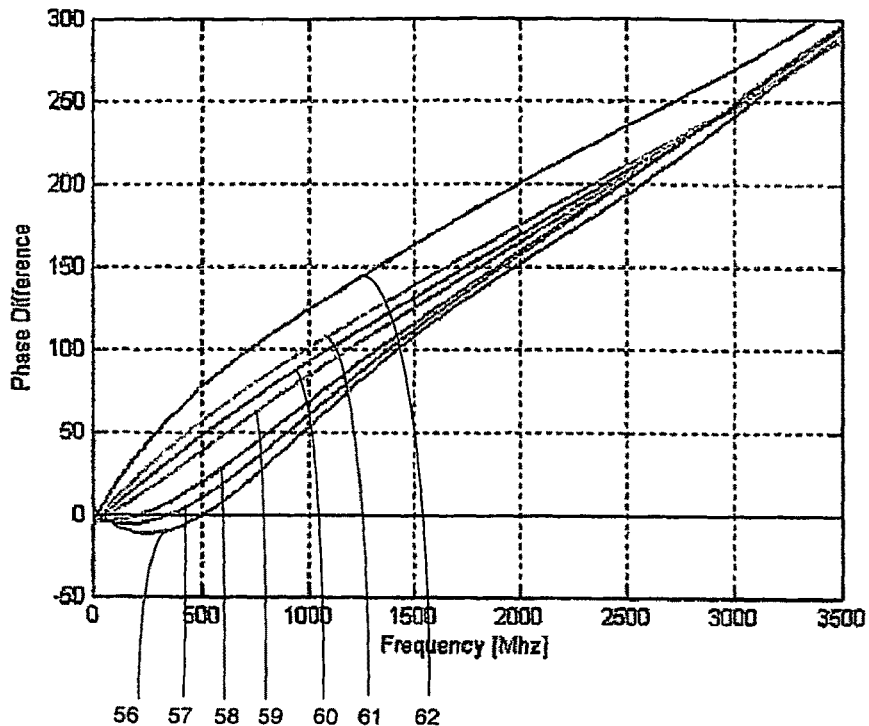
FIG. 15 shows a graph of the measured phase difference vs. frequency for the apparatus of FIG. 2.

FIG. 15 shows the corresponding measured phase difference of the apparatus of FIG. 2 with corresponding values for Z and water salinity.

Figure 18:
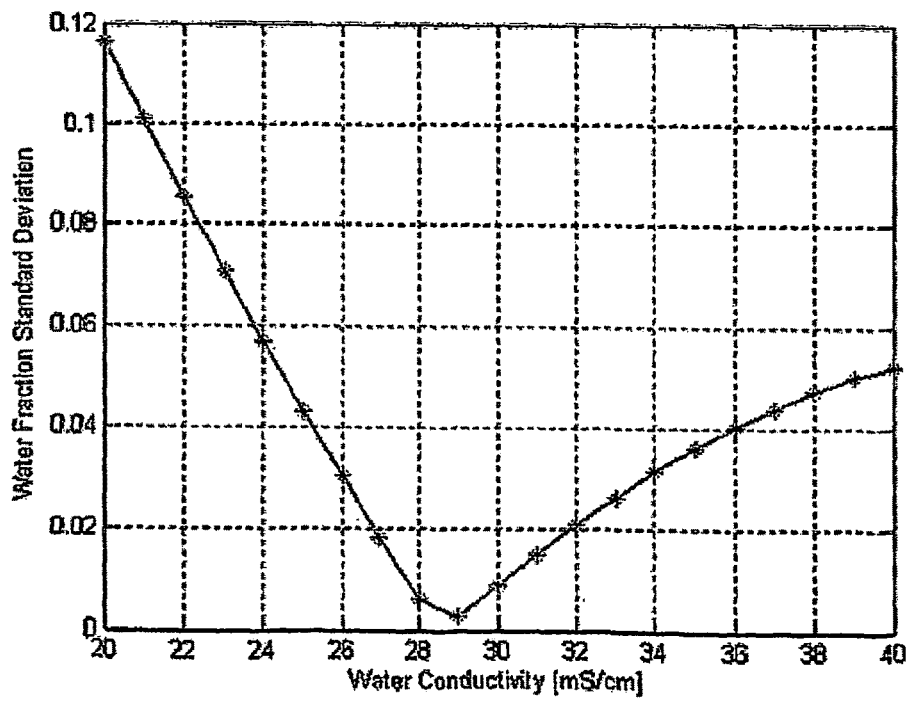
FIG. 18 shows a graph of the calculated water fraction standard deviation vs. water conductivity for the 5 measurement frequencies of FIG. 17.
Figure 19:
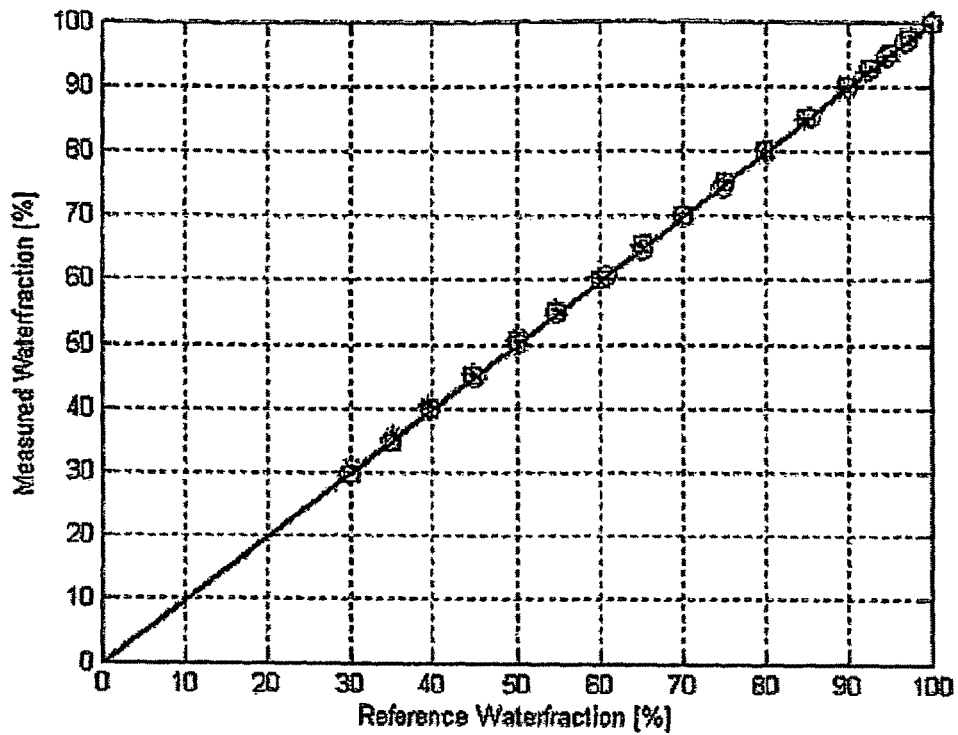
FIG. 19 shows a graph of the measured water fraction vs. the reference water fraction for salinities in the range 0.5%-25% NaCl and water fractions in the liquid phase in the range 30-100%.
Figure 20:
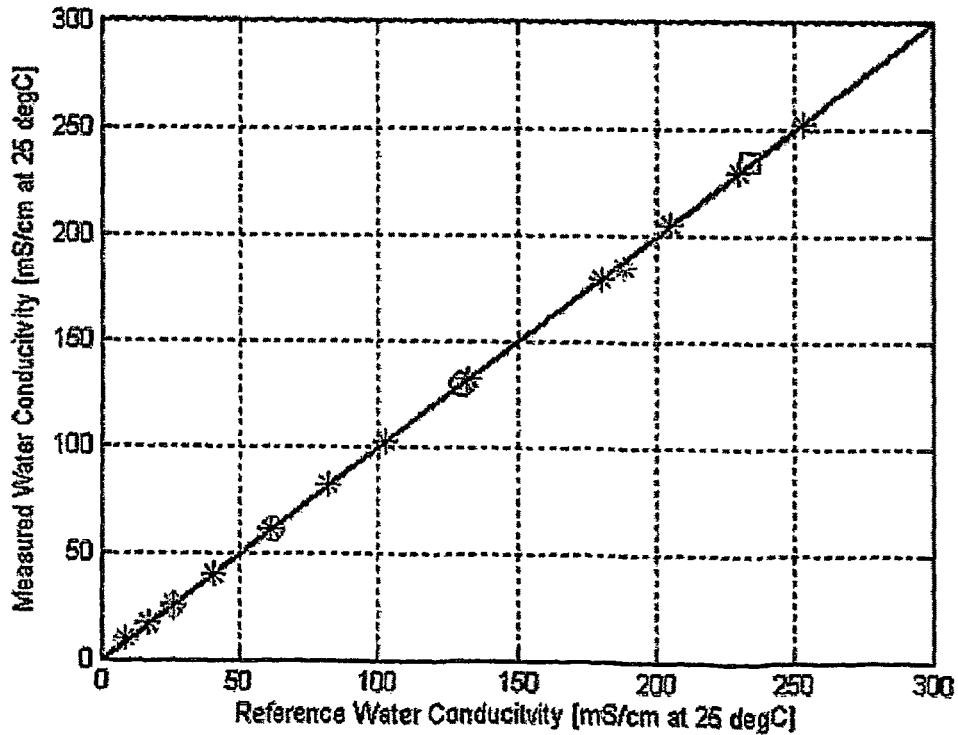
FIG. 20 shows a graph of the measured conductivity vs. the reference conductivity for salinities in the range 0.5%-25% NaCl and water fractions in the liquid phase in the range 30-100%.

The steps involved in order to determine the water conductivity and water (volume) fraction are listed below, ignoring the steps involved in temperature and pressure compensating the measurements:

1) Measure phase difference $\Delta\phi$ at a pre-determined frequency $\omega$
2) Assume a water conductivity $\sigma_{water}$ of $\sigma_1$
3) Calculate real and imaginary dielectric constant of water according to equations 8 and 9
4) Calculate K according to equation 24
5) Calculate conductivity of the oil/water mixture based on the last calculation of the oil fraction and the conductivity of water and oil using equation 23
6) Calculate effective antenna distance Z using equation 22
7) Calculate measured value of $\beta$ using equation 17
8) Calculate the real part of the dielectric constant for the oil/water mixture using equation 25
9) Calculate the imaginary and effective real part of the dielectric constant of the oil/water mixture using equation 24 (imaginary part) and 10 (effective real part)
10) Calculate the volume fraction of water based on the effective real part of the dielectric constant of water oil and the oil/water mixture using equation 11
11) Repeat steps 5-10 until the calculation of the water fraction has converged
12) Repeat steps 2-11 for next measurement frequency
13) Repeat step 2-12 for a wide range of water conductivities ($\sigma_2$, $\sigma_3$, $\sigma_4$, . . . ). The water conductivity is typical varied from the lowest expected water conductivity to the highest expected water conductivity for the fluid flowing in the pipe in steps of say 1-5 mS/cm FIG. 17 shows the resulting water fraction calculation vs. water conductivity for 5 different measurement frequencies calculated according to steps 1-10 at a step size of 1 mS/cm for a water conductivity of 29.1 mS/cm and water fraction of 1.0 inside the pipe. The measurement frequencies used in this case are 800 Mhz, 1100 Mhz, 1500 Mhz, 2100 Mhz and 3400 Mhz respectively 66 67 68 69 and 70. From the graph of FIG. 17 it is seen that the water fraction measurement has a different slope vs. water conductivity for the various measurement frequencies, and the water fraction measurements intercept at a water conductivity value around 29 mS/cm. I.e. for a water conductivity of 29 mS/cm the water fraction measurement is the same for all the measurement frequencies which again provides a measurement of the water fraction and water conductivity. Statistically methods can also be used to determine the point of interception or the point where the spread of the water fraction measurements are at a minimum value. E.g, by calculating the standard deviation between the water fraction measurements at each value of the water conductivity, a curve as shown in FIG. 18 can be derived. FIG. 18 shows a graph of the calculated standard deviation between the calculated water fractions for all the measurement frequencies. As seen on FIG. 18, this graph has a minimum around 29 mS/cm corresponding to the conductivity of the water. One way to determine the location of the minima of the graph of FIG. 18 is to apply a curve fit (such as a $5^{th}$ order polynomial curve fit) to the calculated standard deviation vs. water conductivity and using a computer to numerical find the minima of the curve fitted function. FIG. 15 shows the measured water conductivity for a range of water conductivities.

Based on the above discussion, the following additional steps are involved in determining the water conductivity and water (volume) fraction:

14) Determine the conductivity value for the point of interception between the various water fraction calculations, alternatively determine the conductivity value for the minima point of the water fraction standard deviation curve vs. water conductivity. This conductivity value is a measure of the conductivity of the water of the multiphase mixture
15) Calculate the mean value of the water fraction measurement of all the measurement frequencies and the water conductivity of step 14. The water fraction calculation can be performed according to step 1-12 above using the water conductivity determined in step 11 and the average water fraction from all frequency measurements. This average value for the water fraction is a measure of the water fraction of the multiphase mixture Knowing the conductivity of water, it is possible to determine the salt content of the water. Tables of conductivity vs. salt content can be found in the CRC Handbook of Chemistry and Physics. Algorithms for calculating the conductivity vs. salt content and temperature can be found in Robinson and Stokes, *Electrolyte Solutions* (1959) and A. L. Horvath, *Handbook of Aqueous Electrolyte Solutions* (1985).

Transmission and reflection methods may also be used to measure the fractions and water conductivity as shown in FIG. 4. A combined transmitting and receiving device 40 is located at the pipe wall. The device may either be a clamp-on device transmitting the signals through the pipe wall 1, or transmitting directly into the flow through the pipe wall 1. The device is transmitting a signal, such as a pulse with a given duration and shape. A reflected signal is received from the multiphase mixture and based on an analysis of the reflected signal, the complex dielectric constant of the multiphase mixture can be determined such that the fractions and water conductivity can be obtained according in a similar manner as described above.

An open ended coaxial probe 7 may also be used to measure the fractions and water conductivity as shown in FIG. 3. A coaxial conductor with an inner conductor 7, screen 73 and dielectric insulator 73 is mounted open ended flush with the pipe wall 1 as shown. By transmitting a signal on the coaxial conductor and analyzing the reflected signal on the coaxial line due to the impedance difference between the coaxial cable and the pipe 1 containing the multiphase fluid, the complex dielectric constant of the multiphase mixture can be determined. Based on the measured complex dielectric constant, the fractions and water conductivity of the multiphase mixture can be determined.

The design and working principles of transmission and reflection sensors as shown in FIGS. 3 and 4 is further described in "*Microwave Electronics—measurement and material characterization*" by Chen et. al., Wiley (2004), and "*Permittivity Measurements of Thin Liquid Film Layers using open-ended Coaxial Probes*", Meas. Sci. Technol., 7 (1996), 1164-1173.

Cross correlation techniques are frequently used for measurement of multiphase flow. Techniques for cross correlation flow measurement of multiphase flows are widely described in *Cross Correlation Flow Meters, their design and applications* by M S Beck and A Plaskowski (Adam Hilger, Bristol).

By transmitting an RF carrier transmitted into the flow and measuring the response, the received signal contain information of the variations in the flow caused by amplitude (loss), phase or frequency modulation by the disturbances. By performing the measurements at two sections of the pipe located at a known, one can create two time varying signals that are shifted in time equal to the time it takes the multiphase flow to travel between the two sections.

By cross correlating the two signals using the formula:

$$R_{xy}(\tau) = \lim_{T \to \infty} \frac{1}{T} \int_0^T x(t-\tau) * y(t) \, dt \qquad \text{Equation 26}$$

where x(t) and y(t) are the sampled signals, the time delay τ can be calculated. The time delay τ between the signals x(t) and y(t) is a measure of the time it takes a disturbance in the flow to go from the first to the second pair of antennas.

It is well known that loss due to scatter is highly frequency dependent. Scattering means that a disturbance such as a gas or liquid bubble reradiates parts of the electromagnetic energy such that the energy is lost in the direction of travel towards the receiver. Scattering is normally divided into Rayleigh scattering and Mie scattering which are further described in "*Electromagnetic Mixing Formulas and Applications*" by Ari Sihvola—IEE Electromagnetic Waves series 47.

The Rayleigh scattering of a dielectric sphere such as a liquid droplet is given, according to Sihvola, by the following equation:

$$\sigma_s = \frac{3}{8}\pi a^2 \left(2\pi f \sqrt{\mu_0 \varepsilon_0}\right)^4 \left|\frac{\varepsilon_{inner} - \varepsilon_{outer}}{\varepsilon_{inner} + 2\varepsilon_{outer}}\right| \qquad \text{Equation 27}$$

Where
  $\sigma_s$: Scattering cross section
  a: diameter of the scattering object
  f: frequency
  $\mu_0$: Permeability of free space
  $\varepsilon_0$: Dielectric constant of free space
  $\varepsilon_{inner}$: Dielectric constant of the scatter object
  $\varepsilon_{outer}$: Dielectric constant of the continuous phase As seen from equation 27, the effective scattering section of an object greatly increases with frequency. Consequently by using a high measurement frequency, better measurement resolution can be obtained since the signal is attenuated more in the direction of travel. However, increasing the frequency also reduces the loss in the longitudinal direction of the pipe as shown below.

The fundamental behavior of the pipe, both below and above the cut-off frequency is well described in literature. (e.g. *Fields and Waves in Communication Electronics* by S. Ramo, J R Whinnery aid T. V. Duzer—1984).

The cut-off frequency of the lowest mode in a circular wave guide ($TE_{11}$) is according to Ramo et al given by equation 28 below;

$$f_c = \frac{0.293}{a\sqrt{\mu\varepsilon}} \qquad \text{Equation 28}$$

Where
  $\mu$: Permeability within the sensor (pipe)
  $\varepsilon$: Dielectric constant within the sensor (pipe)
  a: Pipe radius The cut-off wavelength is given by:

$$\lambda_c = 3.41a \qquad \text{Equation 29}$$

Where a: Pipe radius

According to Ramo et al, there is attenuation without phase shift for frequencies below the cut-off frequency of a wave guide and phase shift without attenuation for frequencies above the cutoff frequency, and neither attenuation nor phase shift exactly at cutoff. It is also well known that this fundamental behavior of a wave guide can be used to measure the cut-off frequency of the pipe by measuring the location of the phase shift. Based on the measured frequency, the dielectric constant of the multiphase mixture within the pipe can be derived according to equation 30 below.

$$\varepsilon = \frac{k_2^2}{f_c^2} \qquad \text{Equation 30}$$

Where
  $\varepsilon$: Measured dielectric constant
  $k_2$: Measured cut-off frequency in air
  $f_e$: Measured cut-off frequency of multiphase mixture For the apparatus shown in FIG. 5, a high measurement frequency for performing the cross correlation measurements can be used. The diameter of the smaller pipe section 71, prevents energy traveling and reflected back in the longitudinal direction of the pipe at the cut-off frequency of the sensor, since the sensor has a larger diameter and hence a smaller cut-off frequency as described by equation 28.

However, this method relays on a continuous measurement of the cut-off frequency such that the measurement frequency can be adjusted between each measurement sample. Both the measured loss, phase or the measured cut-off frequency can be used to calculate the cross correlation velocity according to equation 26.

The attenuation coefficient for an electromagnetic wave traveling in the longitudinal direction of the pipe can according to Ramo et.al be calculated according to equation 31 below:

$$\alpha = \frac{2\pi}{\lambda_c}\sqrt{1-\frac{f}{f_c}} \qquad \text{Equation 31}$$

Where
$\alpha$: Attenuation coefficient
$\lambda_C$: Cut-off wavelength
$f_C$: Cut-off frequency
f: Measurement frequency Hence, by using a measurement frequency that is substantially below the cut-off frequency, the ratio $f/f_c$ is much less than 1 such that the attenuation in the longitudinal direction of the pipe becomes substantially independent of frequency. By combining equation 29 and 31 the attenuation coefficient then approximates the constant value:

$$\alpha = \frac{2\pi}{3.41a} \qquad \text{Equation 31}$$

where a: pipe radius

Hence, by measuring or calculating the cut-off frequency of the pipe and selecting a measurement frequency that is substantially below the cut-off frequency, very little energy is traveling in the longitudinal direction of the pipe and hence providing electromagnetic isolation between the two probe pairs in the upstream and downstream cross sections of the pipe.

Signal processing methods for determination of liquid and gas velocities based on cross correlation measurements are well known and examples can be found in "*Simulation of two peaks correlation method for gas-liquid flow velocity measurements*", PhD at UMIST, 1985 bt Corral Davalos, and "*Development of signal interpretation models for multiphase flow rate metering of oil-water-gas flow*", PhD at University of Bergen 1996 by Øivind Midttveit, and "*A pulsed ultrasound cross correlation system for velocity measurement in two component fluids*" PhD at UMIST 1986 by Xu L-A and "*Analysis of space and Time Structures in Two Phase Flow using Capacitance Sensors*", PhD University of Stavanger 1993 by Rune Viggo Time.

A venturi flow meter is commonly used for measurement of flow rate of a multiphase fluid. Any restriction in the pipe will result in a change in the velocity of the multiphase mixture and introduce a pressure drop across the restriction. Based on the theory of fluid dynamics, the square root of the pressure drop is proportional to the total mass flow rate in the pipe. A venturi tube is a structure where the pipe diameter is gradually reduced into a section of the pipe with a smaller diameter. The smaller section may be short or a relative long section. Then the diameter is gradually expanded to the original size of the pipe. Mass flow measurements with such a structure are described in the ISO standards 5167 "*Measurement of fluid flow by means of pressure differential devices inserted in circular cross-section conduits running full*" part 1—general principles and part 4—venturi tubes.

According to ISO 5167-1, the mass flow rate can be calculated as:

$$Qm = \frac{C}{\sqrt{1-\beta^4}}\frac{\pi}{4}d^2\sqrt{2\rho\Delta\rho} \qquad \text{Equation 32}$$

where:
Qm=Total mass flow rate
C=Discharge coefficient
$\beta$=Diameter ratio between venturi throat and pipe
d=Diameter of venturi throat
$\Delta$p=Measured pressure drop between inlet and venturi throat
$\rho$=Density of the multiphase mixture The adoption of venturi tubes for multiphase and wetgas flow conditions are further described in "*Design of a flow metering process for two-phase dispersed flows*", Int. J. Multiphase Flow vol 22, No 4, pp 713-732, "*A study of the performance of Venturi meters in multiphase flow*", by Hall, Reader-Harris, and Millington, 2$^{nd}$ North American Conference on Multiphase Technology and "*Liquid Correction of Venturi Meter Readings in Wet Gas Flow*", by Rick de Leeuw, North Sea Flow Measurement Workshop—1997.

The invention claimed is:

1. A method for determining the water conductivity of a multi-component mixture of gas and at least one liquid containing water in a pipe, the method comprising the following steps:
   a. performing electromagnetic phase or loss measurements at at least two measurement frequencies within the range of 1 MHz to 10000 MHz in said pipe near the pipe wall at a first location where said mixture predominantly contains gas and at a second location where said mixture predominantly contains liquid,
   b. determining the temperature of the multi-component mixture,
   c. calculating using a computer and a mathematical program the ratio between at least one of the loss or phase measurements from said first location and the corresponding one of the loss or phase measurements from said second location, and
   d. determining the conductivity of the water contained in the multi-component mixture based on the temperature determined in step b, an empirically determined relationship between the ratio calculated in step c and the conductivity of water.

2. A method according to claim 1, wherein the measurements are performed in a substantially horizontal pipe section.

3. A method according to claim 2, wherein said pipe section has an enlarged cross-sectional area.

4. A method according to claim 2, wherein said pipe has a top and a bottom, said method further comprising locating said first location at said top of the pipe and locating said second location at said bottom of the pipe.

5. A method according to claim 1, wherein electromagnetic measurements are performed based on measurement of reflected electromagnetic energy from the pipe.

6. A method according to claim 5, wherein the measurements are performed on a sinusoidal signal.

7. A method according to claim 5, wherein measurements are performed on a pulse shaped signal.

8. A method according to claim 1, wherein the velocity of the multi-component mixture is determined.

9. A method according to claim 8, wherein the velocity of the multi-component mixture is determined based on cross-correlation techniques.

10. A method according to claim 8, wherein the velocity of the multi-component mixture is determined based on a measurement of pressure drop across a narrow passage in the pipe.

11. A method according to claim 1, wherein electromagnetic measurements are performed based on measurement of transmission loss between a sending and receiving antenna inside the pipe.

12. A method according to claim 1, wherein electromagnetic measurements are performed based on measurement of phase differences between two receiving antennas located different distances from a transmitting antenna.

13. A method according to claim 1, wherein the water fraction of the liquid is determined.

14. An apparatus for determining the water conductivity of a multi-component mixture of gas and at least one liquid containing water in a pipe, the apparatus comprising a tubular section and the following elements:
   a. means for performing electromagnetic phase or loss measurements at at least two measurement frequencies within the range of 1 MHz to 10000 MHz near the wall of the tubular section at a first location where the mixture predominantly contains gas and at a second location where the mixture predominantly contains liquid,
   b. means for determining the temperature of the multi-component mixture,
   c. a computer means for calculating the ratio between at least one of the loss or phase measurements from said first location and the corresponding one of the loss or phase measurements from said second location,
   d. a computer and a mathematical program for calculating the conductivity of the water contained in the multi-component mixture based on the temperature determined by the means of part b, the result of part c, and an empirically derived calibration curve for the relationship between the ratio defined in part c and the conductivity of water.

15. An apparatus according to claim 14, wherein the tubular section is substantially a horizontal pipe section.

16. An apparatus according to claim 15, wherein said tubular section has an enlarged cross-sectional area.

17. An apparatus according to claim 15, comprising electronic means for transmitting electromagnetic energy at at least two frequencies on two transmitting antennas and recording received electromagnetic energy for the frequencies at at least two receiving antennas.

18. An apparatus according to claim 14, comprising means for measuring the velocity of the multi-component mixture.

19. An apparatus according to claim 18, comprising means for measuring said velocity by cross-correlating measurements performed in two cross-sections of the tubular section.

20. An apparatus according to claim 18, comprising means for measuring said velocity in a narrow passage of the tubular section.

21. An apparatus according to claim 14, comprising electronic means for transmitting electromagnetic energy and receiving reflected energy from the pipe.

22. An apparatus according to claim 14, comprising a mathematical program for calculating the water fraction of the liquid.

* * * * *